United States Patent [19]

Göschke

[11] Patent Number: 5,659,065

[45] Date of Patent: Aug. 19, 1997

[54] ALPHA-AMINOALKANOIC ACIDS AND REDUCTION PRODUCTS

[75] Inventor: Richard Göschke, Bottmingen, Switzerland

[73] Assignee: Novartis Corporation, Tarrytown, N.Y.

[21] Appl. No.: 416,240

[22] Filed: Apr. 4, 1995

[30] Foreign Application Priority Data

Apr. 18, 1994 [CH] Switzerland .................. 1169/94
Jan. 30, 1995 [CH] Switzerland .................. 247/95

[51] Int. Cl.$^6$ .................. C07C 219/28; C07C 223/02; C07C 229/06; C07C 229/08; C07C 229/10; C07C 229/36

[52] U.S. Cl. .................. 560/29; 544/59; 544/60; 544/111; 544/122; 544/146; 544/162; 544/165; 544/242; 544/296; 544/359; 544/360; 544/379; 544/398; 546/174; 546/176; 546/208; 546/210; 546/212; 546/232; 546/293; 546/334; 546/335; 546/270.4; 546/272.7; 546/276.4; 546/280.4; 546/283.4; 548/146; 548/339.1; 548/518; 548/527; 548/566; 549/362; 560/24; 560/27; 560/38; 568/423; 568/424; 568/704; 568/706

[58] Field of Search .................. 560/29, 38, 24; 544/59, 60, 111, 122, 146, 162, 165, 242, 296, 359, 360, 379, 398; 546/174, 176, 208, 210, 212, 232, 275, 276, 277, 293, 334, 335; 548/146, 339.1, 518, 527, 566; 549/362; 568/423, 424, 704, 706

[56] References Cited

U.S. PATENT DOCUMENTS 3,264,279  8/1966  Schwyzer et al. .................. 560/29
3,988,341  10/1976  Saari et al. .................. 560/38

OTHER PUBLICATIONS

Uremura "Sterecontrolled Synthesis of (2R, 3R, 5R, 13S, 14 R)–(t)–aplisiasphingosine a Marine Terpenoid" Agc Biol Chem 51(7) 1987.

Hadrami et al "Synthesis of (2S 4S, 6S)–2–Amino–6–Hydroxy–4–Methyl–8–Oxodecanoic Acid and (4S, E)–H–Methylhex–2–Enoic Acid Constituents of Leucinostatines", Tetrahedron Letters, vol. 32, No. 32, pp. 3985–3988 (1991).

Bernasconi et al "Synthesis of (2S, 4S)– and (2R, 4S)–2–Amino–4–methylexanoic Acid (Homoleucine) (*)" Gazetta Chimica, Ital. vol. 107, pp. 95–99 (1977).

Journal of High Resolution Chromatography, vol. 16 pp. 568–586 (1993).

Broxterman "Synthesis of (Optically Active) Sulfur–Containing Trifunctional Amino Acids by Radical Addition to (Optically Active) Unsaturated Amino Acids" J. Org. Chem. vol. 57, pp. 6286–6294 (1992).

Taguchi "An Efficient Resolution of 3–Trifluoromethyl-y–butyrolactone and Its Conversion to 5, 5, 5–Trifluorleucinol" Terrahedron Letters, vol. 27, No. 42, pp. 5117–5120 (1986).

Schollkopf et al "Enantioselective Synthesis of (R)–Amino Acids Using L–Valine as Chiral Agent [**]" Agnew Chem. Lat. Eda. vol. 20, pp.798–799 (1981).

Chemical abstracts accession No. 101:191208, Tokyo Tanabe Co., Ltd., registry No. 92754–70–6 Jun. 1984.

Chemical abstract accession No. 121:134724, Crisp et al., Tetrahedron, vol. 50, No. 10, registry No. 1567894–53–0 1994.

Meakin et al., J. Pharm. Pharmacology, Chemical abstracts registry No. 103905–69–7 Nov. 1959.

Meakin et al., J. Pharm. Pharmocology, Chemical abstracts registry No. 102450–23–7 Nov. 1959.

Meakin et al., J. Pharm. Pharmocology, Chemical abstracts registry No. 92987–67–2 Nov. 1959.

Meakin et al., J. Pharm. Pharmocology, Chemical abstracts registry No. 100535–58–8 Nov. 1959.

Meakin et al., J. Pharm. Pharmocology, Chemical abstracts registry No. 100387–30–2 Nov. 1959.

Montforts, "A Directed Synthesis of the Chlorin System" Angew Chem. Int. Ed. Engl. 20(9):778–779 (1981).

Schöllkopf, "A Symmetric Syntheses of Amino Acids Via Metalated Bis–Lactim Ethers of 2,5–Diketopiperazines" Pure & Appl. Chem. 55(11):1799–1806 (1983).

Groth et al. "A Symmetric Syothesis via Heterocyclic Intermediates, 1 11[1] Synthesis of Tert–Leucine and Related Amino Acids" Liebigs Ann. Chem. :715–719 (1993).

Blake et al. "Pyrazine Chemistry, Part IV.$^1$ Thermal [1,4] Eliminations from 3.6–Di–hydropyrazines"J. C. S.: Perkin I.2 (830): 2494–2497 (1972).

Primary Examiner—Robert E. Sellers
Attorney, Agent, or Firm—Marla J. Mathias; Gregory D. Ferraro

[57]  ABSTRACT

Compounds of formula I

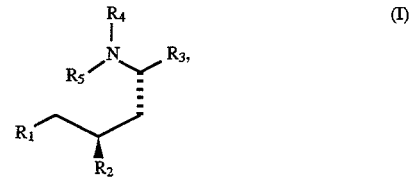

wherein $R_1$ is an aliphatic, cycloaliphatic, cycloaliphatic-aliphatic, aromatic or heteroaromatic radical, a hydroxy group that is aliphatically, araliphatically or heteroarylaliphatically etherified or protected by a hydroxy-protecting group, or an aliphatically etherified mercapto group, and $R_2$ is an aliphatic, cycloaliphatic, cycloaliphatic-aliphatic, araliphatic or heteroarylaliphatic radical, or $R_1$ and $R_2$ together form a divalent aliphatic radical, $R_3$ is free or aliphatically, araliphatically or aromatically esterified carboxy, formyl or hydroxymethyl, $R_4$ is hydrogen, an aliphatic or araliphatic radical or an amino-protecting group, and $R_5$ is hydrogen or an aliphatic radical, and the salts thereof can be used as intermediates in the preparation of medicinal active ingredients.

5 Claims, No Drawings

ALPHA-AMINOALKANOIC ACIDS AND REDUCTION PRODUCTS

The invention relates to compounds of formula I

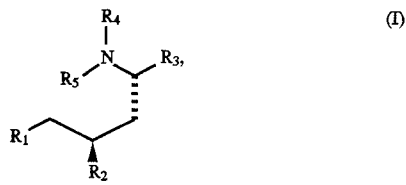

wherein

- $R_1$ is an aliphatic, cycloaliphatic, cycloaliphatic-aliphatic, aromatic or heteroaromatic radical, a hydroxy group that is aliphatically, araliphatically or heteroarylaliphatically etherified or protected by a hydroxy-protecting group, or an aliphatically etherified mercapto group, and
- $R_2$ is an aliphatic, cycloaliphatic, cycloaliphatic-aliphatic, araliphatic or heteroarylaliphatic radical, or
- $R_1$ and $R_2$ together form a divalent aliphatic radical,
- $R_3$ is free or aliphatically, araliphatically or aromatically esterified carboxy, formyl or hydroxymethyl,
- $R_4$ is hydrogen, an aliphatic or araliphatic radical or an amino-protecting group, and
- $R_5$ is hydrogen or an aliphatic radical, and to the salts thereof, to processes for the preparation of the compounds according to the invention and to the use thereof as intermediates in the preparation of medicinal active ingredients.

Aliphatic radicals are, for example, lower alkyl radicals, and in the case of $R_1$ also lower alkenyl radicals.

Cycloaliphatic radicals are, for example, cycloalkyl radicals.

Cycloaliphatic-aliphatic radicals are, for example, cycloalkyl-lower alkyl radicals.

Araliphatic radicals are, for example, unsubstituted or substituted phenyl- or naphthyl-lower alkyl radicals. Suitable substituents are, for example, 1, 2 or 3, especially 1 or 2, substituents selected, for example, from lower alkyl, lower alkoxy, halogen and/or trifluoromethyl.

Aromatic radicals are, for example, unsubstituted or substituted phenyl or naphthyl radicals. Suitable substituents of aromatic radicals $R_1$ are, for example, 1, 2 or 3, especially 2 or 3, substituents selected from amino-lower alkoxy, amino-lower alkyl, aryl-lower alkoxy, carbamoyl-lower alkoxy, carbamoyl-lower alkyl, carboxy-lower alkoxy, carboxy-lower alkoxy, carboxy-lower alkyl, cyano-lower alkoxy, cyano-lower alkyl, cycloalkoxy, cycloalkoxy-lower alkoxy, cycloalkoxy-lower alkyl, cycloalkyl, di-lower alkylamino, di-lower alkylamino-lower alkoxy, di-lower alkylamino-lower alkyl, optionally partially hydrogenated heteroaryl-lower alkoxy, optionally N-oxidised pyridylthio-lower alkoxy, optionally N-oxidised pyridylthio-lower alkyl, halo-(hydroxy)-lower alkoxy, halogen, hydroxy, hydroxy-lower alkoxy, hydroxy-lower alkyl, imidazolylthio-lower alkoxy, imidazolylthio-lower alkyl, morpholino-lower alkoxy, morpholino-lower alkyl, N-mono- or N,N-di-lower alkylcarbamoyl-lower alkoxy, N-mono- or N,N-di-lower alkylcarbamoyl-lower alkyl, optionally N-oxidised pyridyl-lower alkyl, N'-lower alkylpiperazino- or N'-lower alkanoylpiperazino-lower alkoxy, N'-lower alkylpiperazino- or N'-lower alkanoylpiperazino-lower alkyl, naphthyl, naphthyl-lower alkoxy, lower alkanoylamino-lower alkoxy, lower alkanoylamino-lower alkyl, lower alkanoyl-lower alkoxy, lower alkanoyloxy-lower alkyl, lower alkanesulfonyl(hydroxy)-lower alkoxy, lower alkanesulfonylamino-lower alkoxy, lower alkanesulfonylamino-lower alkyl, lower alkanesulfonyl-lower alkoxy, lower alkanesulfonyl-lower alkyl, lower alkenyloxy, lower alkenyloxy-lower alkoxy, lower alkenyloxy-lower alkyl, lower alkoxy, lower alkoxycarbonylamino-lower alkoxy, lower alkoxycarbonylamino-lower alkyl, lower alkoxycarbonyl-lower alkoxy, lower alkoxycarbonyl-lower alkyl, lower alkoxyimino-lower alkyl, lower alkoxy-lower alkenyl, lower alkoxy-lower alkenyloxy, lower alkoxy-lower alkoxy, lower alkoxy-lower alkoxy-lower alkyl, lower alkoxy-lower alkyl, lower alkyl, lower alkylamino, lower alkylamino-lower alkoxy, lower alkylamino-lower alkyl, lower alkylthio-(hydroxy)-lower alkoxy, lower alkylthio-lower alkoxy, lower alkylthio-lower alkoxy, lower alkylthio-lower alkyl, oxo-lower alkoxy, piperazino-lower alkoxy, piperazino-lower alkyl, piperidino-lower alkoxy, piperidino-lower alkyl, polyhalo-lower alkanesulfonylamino-lower alkoxy, polyhalo-lower alkanesulfonylamino-lower alkyl, polyhalo-lower alkoxy, polyhalo-lower alkyl, pyrimidinylthio-lower alkoxy, pyrimidinylthio-lower alkoxy, pyrimidinylthio-lower alkyl, pyrrolidino-lower alkoxy, pyrrolidino-lower alkyl, S,S-dioxothiomorpholino-lower alkoxy, S,S-dioxothiomorpholino-lower alkyl, S-oxothiomorpholino-lower alkoxy, S-oxothiomorpholino-lower alkyl, thiazolylthio-lower alkoxy, thiazolinylthio-lower alkoxy, thiazolylthio-lower alkyl, thiazolinylthio-lower alky and/or thiomorpholino and fused-on benzo or cyclohexeno rings.

Aromatic radicals $R_1$ are, for example, those of formula

wherein

- $R_6$ is hydrogen, hydroxy, lower alkoxy, cycloalkoxy, lower alkoxy-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy,
- $R_7$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoylamino-lower alkyl, lower alkoxycarbonylamino-lower alkyl, lower alkoxyimino-lower alkyl, amino-lower alkoxy, lower alkylamino-lower alkoxy, di-lower alkylamino-lower alkoxy, lower alkanoylamino-lower alkoxy, lower alkoxycarbonylamino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, carbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R_8$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolylthio-lower alkyl or thiazolinylthio-lower alkyl, imidazolylthio-lower alkyl, optionally N-oxidised pyridylthio-lower alkyl, pyrimidinylthio-lower alkyl, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl, cyano-lower alkyl, carboxy-lower alkyl, lower alkoxycarbonyl-lower alkyl, carbamoyl-lower alkyl, N-mono- or N,N-di-lower alkylcarbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-, di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino-lower alkoxy, cyano-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy or together with $R_9$ is lower alkylenedioxy or a fused-on benzo or cyclohexeno ring, $R_9$ together with $R_8$ is lower alkylenedioxy or a fused-on benzo or cyclohexeno ring or is hydrogen, lower alkyl, hydroxy, lower alkoxy or cycloalkoxy.

Heteroaromatic radicals are, for example, unsubstituted or substituted 5- or 6-membered monocyclic heteroaryl radicals or unsubstituted or substituted heteroaryl radicals composed of 5- or 6-membered rings, such as furyl, thienyl, pyridyl, pyrimidinyl, indolyl or quinolinyl. Suitable substituents are, for example, 1, 2 or 3, especially 1 or 2, substituents selected, for example, from lower alkyl, lower alkoxy, halogen and/or trifluoromethyl.

Optionally hydrogenated heteroaryl-lower alkoxy is, for example, optionally partially hydrogenated or N-oxidised pyridyl-lower alkoxy, thiazolyl-lower alkoxy or especially morpholino-lower alkoxy.

Aliphatically etherified hydroxy groups are, for example, lower alkoxy or lower alkenyloxy groups.

Araliphatically etherified hydroxy groups are, for example, phenyl-lower alkoxy groups that are unsubstituted or substituted in the phenyl moiety. Suitable substituents are, for example, 1, 2 or 3, especially 1 or 2, substituents selected, for example, from lower alkyl, lower alkoxy, halogen and/or trifluoromethyl.

Heteroarylaliphatically etherified hydroxy groups are, for example, hydroxy groups etherified by an unsubstituted or substituted 5- or 6-membered monocyclic heteroaryla-liphatic alcohol or an unsubstituted or substituted heteroary-laliphatic alcohol composed of 5- or 6-membered rings, such as unsubstituted or substituted furyl-lower alkoxy, thienyl-lower alkoxy, pyridyl-lower alkoxy or quinolinyl-lower alkoxy groups. Suitable substituents are, for example, 1, 2 or 3, especially 1 or 2, substituents selected, for example, from lower alkyl, lower alkoxy, halogen and/or trifluoromethyl.

Hydroxy groups protected by a hydroxy-protecting group are protected, for example, by an acyl group derived from an aliphatic or aromatic carboxylic acid or an aliphatic or araliphatic semi-ester of carbonic acid or by an aliphatically and/or araliphatically substituted silyl group. Examples that may be mentioned are lower alkanoyloxy, tri-halo-lower alkanoyloxy, such as trifluoroacetyloxy, unsubstituted or substituted, for example lower alkyl-, lower alkoxy-, halo-, trifluoromethyl- and/or nitro-substituted, benzoyloxy or phenyl-lower alkoxycarbonyloxy groups, tri-lower alkylsi-lyloxy and benzyl(di-lower alkyl)silyloxy.

Aliphatically etherified mercapto groups are, for example, lower alkylthio groups.

Araliphatic radicals are, for example, phenyl-lower alkyl or naphthyl-lower alkyl radicals. Suitable substituents are, for example, 1, 2 or 3, especially 1 or 2, substituents selected, for example, from lower alkyl, lower alkoxy, halogen and/or trifluoromethyl.

Heteroarylaliphatic radicals are, for example, unsubstituted or substituted 5- or 6-membered monocyclic heteroaryl-lower alkyl radicals or unsubstituted or substituted heteroaryl-lower alkyl radicals composed of 5- or 6-membered rings, such as furyl-lower alkyl, thienyl-lower alkyl, optionally partially hydrogenated or N-oxidised pyridyl-lower alkyl, pyrimidinyl-lower alkyl or quinolinyl-lower alkyl. Suitable substituents are, for example, 1, 2 or 3, especially 1 or 2, substituents selected, for example, from lower alkyl, lower alkoxy, halogen and/or trifluoromethyl.

Divalent aliphatic radicals formed by $R_1$ and $R_2$ together are, for example, lower alkylene radicals the free valencies of which originate from carbon atoms that are adjacent to one another or in the 1,3-, 1,4- or 1,5-position relative to one another.

Free or aliphatically, araliphatically or aromatically esterified carboxy is, for example, carboxy, lower alkoxycarbonyl, lower alkenyloxycarbonyl or unsubstituted or substituted phenyl-lower alkoxycarbonyl or phenyloxycarbonyl radicals. Suitable substituents of the latter two are, for example, 1, 2 or 3, especially 1 or 2, substituents selected, for example, from lower alkyl, lower alkoxy, halogen and/or trifluoromethyl.

Amino-protecting groups are, for example, acyl groups derived from an aliphatic or aromatic carboxylic acid or from an aliphatic or araliphatic semi-ester of carbonic acid, or aliphatically and/or araliphatically substituted silyl groups. Examples that may be mentioned are lower alkanoyl, tri-halo-lower alkanoyl, such as trifluoroacetyl, unsubstituted or substituted, for example lower alkyl-, lower alkoxy-, halo-, trifluoromethyl- and/or nitro-substituted, benzoyl or phenyl-lower alkoxycarbonyl groups, tri-lower alkylsilyl and benzyl(di-lower alkyl)silyl.

Hereinbefore and hereinafter, lower radicals and compounds are to be understood as being, for example, those having up to and including 7, preferably up to and including 4, carbon atoms.

Amino-lower alkyl is, for example, amino-$C_1$–$C_4$alkyl, such as 2-aminoethyl, 3-aminopropyl or 4-aminobutyl.

Aryl-lower alkoxy is, for example, phenyl-$C_1$–$C_4$alkoxy, such as benzyloxy, 1- or 2-phenylethoxy, 3-phenylpropyloxy or 4-phenylbutyloxy.

Benzyl(di-lower alkyl)silyl is, for example, benzyl(di-$C_1$–$C_4$alkyl)silyl, such as especially benzyl(dimethyl)silyl.

Carbamoyl-lower alkoxy is, for example, carbamoyl-$C_1$–$C_4$alkoxy, such as carbamoylmethoxy, 2-carbamoylethoxy, 3-carbamoylpropyloxy or 4-carbamoylbutyloxy, especially carbamoylmethoxy.

Carbamoyl-lower alkyl is, for example, carbamoyl-$C_1$–$C_4$, such as carbamoylmethyl, 2-carbamoylethyl, 3-carbamoylpropyl, 2-(3-carbamoyl)propyl, 2-carbamoylpropyl, 3-(1-carbamoyl)propyl, 2-(2-carbamoyl)propyl, 2-(carbamoyl-2-methyl)propyl, 4-carbamoylbutyl, 1-carbamoylbutyl, 1-(1-carbamoyl-2-methyl)butyl or 3-(4-carbamoyl-2-methyl)butyl.

Carboxy-lower alkoxy is, for example, carboxy-$C_1$–$C_4$alkoxy, such as carboxymethoxy, 2-carboxyethoxy, 2- or 3-carboxypropyloxy or 4-carboxybutyloxy, especially carboxymethoxy.

Carboxy-lower alkyl is, for example, carboxy-$C_1$–$C_4$alkyl, such as carboxymethyl, 2-carboxyethyl, 2- or 3-carboxypropyl, 2-carboxy-2-methyl-propyl, 2-carboxy-2-ethyl-butyl or 4-carboxybutyl, especially carboxymethyl.

Quinolinyl-lower alkoxy is, for example, quinolinyl-$C_1$–$C_4$alkoxy, such as quinolinylmethoxy, 2-quinolinylethoxy, 3-quinolinylpropyloxy or 4-quinolinylbutyloxy, especially quinolinylmethoxy.

Cyano-lower alkoxy is, for example, cyano-$C_1$–$C_4$alkoxy, such as cyanomethoxy, 2-cyanoethoxy, 2- or 3-cyanopropyloxy or 4-cyanobutyloxy, especially cyanomethoxy.

Cyano-lower alkyl is, for example, cyano-$C_1$–$C_4$alkyl, such as cyanomethyl, 2-cyanoethyl, 2- or 3-cyanopropyl, 2-cyano-2-methyl-propyl, 2-cyano-2-ethyl-butyl or 4-cyanobutyl, especially cyanomethyl.

Cycloalkoxy is, for example, 3- to 8-membered, especially 3- to 6-membered, cycloalkoxy, such as cyclopropyloxy, cyclobutyloxy, cyclopentyloxy or cyclohexyloxy.

Cycloalkoxy-lower alkoxy is, for example, 3- to 8-membered, especially 3- to 6-membered, cycloalkoxy-$C_2$–$C_4$alkoxy, such as 2-cyclopropyloxyethoxy, 2-cyclobutyloxyethoxy, 2-cyclopentyloxyethoxy or 2-cyclohexyloxyethoxy.

Cycloalkoxy-lower alkyl is, for example, 3- to 8-membered, especially 3- to 6-membered, cycloalkoxy-$C_2$–$C_4$alkyl, such as cyclopropyloxymethyl, cyclobutyloxymethyl, cyclopentyloxymethyl or cyclohexyloxymethyl.

3- to 8-Membered cycloalkyl is, for example, 3- to 8-membered, especially 3- to 6-membered, cycloalkyl, such as cyclopropyl, cyclobutyl, cyclopentyl or cyclohexyl.

Cycloalkyl-lower alkyl is, for example, 3- to 8-membered, and in the case of $R_1$ especially 5- to 7-membered, cycloalkyl-$C_1$–$C_4$alkyl, such as cyclopentylmethyl, cyclohexylmethyl or cycloheptylmethyl, and in the case of $R_2$ especially 3- to 5-membered cycloalkyl-$C_1$–$C_4$alkyl, such as cyclopropylmethyl, cyclobutylmethyl or cyclohexylmethyl.

Di-lower alkylamino is, for example, di-$C_1$–$C_4$alkylamino, such as dimethylamino, N-methyl-N-ethylamino, diethylamino, N-methyl-N-propylamino or N-butyl-N-methylamino.

Di-lower alkylamino-lower alkoxy is, for example, N,N-di-$C_1$–$C_4$alkylamino-$C_1$–$C_4$alkoxy, such as 2-dimethylaminoethoxy, 3-dimethylaminopropyloxy, 4-dimethylaminobutyloxy, 2-diethylaminoethoxy, 2-(N-methyl-N-ethyl-amino)ethoxy or 2-(N-butyl-N-methyl-amino)ethoxy.

Di-lower alkylamino-lower alkyl is, for example, N,N-di-$C_1$–$C_4$alkylamino-$C_1$–$C_4$alkyl, such as 2-dimethylaminoethyl, 3-dimethylaminopropyl, 4-dimethylaminobutyl, 2-diethylaminoethyl, 2-(N-methyl-N-ethyl-amino)ethyl or 2-(N-butyl-N-methyl-amino)ethyl.

Furyl-lower alkoxy-lower alkoxy is, for example, furyl-$C_1$–$C_4$alkoxy-$C_2$–$C_4$alkoxy, such as 2-(furylmethoxy)ethoxy, 2-(2-furylethoxy)ethoxy, 3-(furylmethoxy)propyloxy or 4-(furylmethoxy)butyloxy.

Furyl-lower alkyl is, for example, furyl-$C_1$–$C_4$alkyl, such as furylmethyl, 1-furylethyl, 2-furylethyl, 3-furylpropyl or 4-furylbutyl.

Optionally partially hydrogenated or N-oxidised pyridyl-lower alkyl is, for example, optionally partially hydrogenated pyridyl- or N-oxidopyridyl-$C_1$–$C_4$alkyl, such as pyridyl- or N-oxidopyridyl-methyl, 2-pyridylethyl, 2- or 3-pyridylpropyl or 4-pyridylbutyl, especially 3- or 4-pyridylmethyl.

Optionally N-oxidised pyridylthio-lower alkoxy is, for example, pyridylthio-$C_1$–$C_4$alkoxy or N-oxidopyridylthio-$C_1$–$C_4$alkoxy, such as pyridylthio- or N-oxidopyridylthio-methoxy, 2-pyridylthioethoxy, 2- or 3-pyridylthiopropyloxy or 4-pyridylthiobutyloxy, especially 3- or 4-pyridylthiomethoxy.

Optionally N-oxidised pyridylthio-lower alkyl is, for example, pyridylthio-$C_1$–$C_4$alkyl or N-oxidopyridylthio-$C_1$–$C_4$alkyl, such as pyridylthio- or N-oxidopyridylthio-methyl, 2-pyridylthioethyl, 2- or 3-pyridylthiopropyl or 4-pyridylthiobutyl, especially 3- or 4-pyridylthiomethyl.

Halogen is, for example, halogen having an atomic number of up to and including 35, such as chlorine or bromine, also fluorine.

Halo-(hydroxy)-lower alkoxy is, for example, halo-$C_2$–$C_7$(hydroxy)alkoxy, especially halo-$C_2$–$C_4$(hydroxy)alkoxy, such as 3-halo-, such as 3-chloro-2-hydroxy-propyloxy.

Hydroxy-lower alkoxy is, for example, hydroxy-$C_2$–$C_7$-alkoxy, especially hydroxy-$C_2$–$C_4$-alkoxy, such as 2-hydroxybutyloxy, 3-hydroxypropyloxy or 4-hydroxybutyloxy.

Hydroxy-lower alkyl is, for example, hydroxy-$C_2$–$C_7$alkyl, especially hydroxy-$C_2$–$C_4$alkyl, such as 2-hydroxyethyl, 3-hydroxypropyl or 4-hydroxybutyl.

Imidazolyl-lower alkoxy is, for example, imidazolyl-$C_1$–$C_4$alkoxy, such as imidazol-4-ylmethoxy, 2-(imidazol-4-yl)ethoxy, 3-(imidazol-4-yl)propyloxy or 4-(imidazol-4-yl)butyloxy.

Imidazolyl-lower alkyl is, for example, imidazolyl-$C_1$–$C_4$alkyl, such as imidazol-4-ylmethyl, 2-(imidazol4-yl)ethyl, 3-(imidazol-4-yl)propyl or 4-(imidazol-4-yl)butyl.

Imidazolylthio-lower alkoxy is, for example, imidazolylthio-$C_1$–$C_4$alkoxy, such as imidazolthio-4- ylmethoxy, 2-(imidazolthio-4-yl)ethoxy, 3-(imidazolthio-4-yl)propyloxy or 4-(imidazolthio-4-yl)butyloxy.

Imidazolylthio-lower alkyl is, for example, imidazolylthio-$C_1$–$C_4$alkyl, such as imidazolthio-4-ylmethyl, 2-(imidazolthio-4-yl)ethyl, 3-(imidazolthio-4-yl)propyl or 4-(imidazolthio-4-yl)butyl.

Morpholino-lower alkoxy may be N-oxidised and is, for example, morpholino-$C_1$–$C_4$alkoxy, such as 1-morpholinomethyl, 3-morpholinopropyloxy, or 1-(morpholino-2-methyl)propyloxy.

Morpholino-lower alkyl may be N-oxidised and is, for example, morpholino-$C_1$–$C_4$alkyl, such as morpholinomethyl, 2-morpholinoethyl, 3-morpholinopropyl or 1- or 2-(4-morpholino)butyl.

N'-Lower alkanoylpiperazino-lower alkoxy is, for example, N'-lower alkanoylpiperazino-$C_1$–$C_4$alkoxy, such as 4-acetylpiperazinomethoxy.

N'-Lower alkanoylpiperazino-lower alkyl is, for example, N'-$C_2$–$C_7$alkanoylpiperazino-$C_1$–$C_4$alkyl, such as 4-acetylpiperazinomethyl.

N'-Lower alkylpiperazino-lower alkyl is, for example, N'-$C_1$–$C_4$alkylpiperazino-$C_1$–$C_4$alkyl, such as 4-methylpiperazinomethyl.

Di-lower alkylcarbamoyl-lower alkoxy is, for example, N,N-di-$C_1$–$C_4$alkylcarbamoyl-$C_1$–$C_4$-alkoxy, such as methyl- or dimethyl-carbamoyl-$C_1$–$C_4$alkoxy, such as N,N-dimethylcarbamoylmethoxy, 2-(N,N-dimethylcarbamoyl)ethoxy, 3-(N,N-dimethylcarbamoyl)propyloxy or 4-(N,N-dimethylcarbamoyl)butyloxy, especially N,N-dimethylcarbamoylmethoxy.

Di-lower alkylcarbamoyl-lower alkyl is, for example, N,N-di-$C_1$–$C_4$alkylcarbamoyl-$C_1$–$C_4$alkyl, such as 2-dimethylcarbamoylethyl, 3-dimethylcarbamoylpropyl, 2-dimethylcarbamoylpropyl, 2-(dimethylcarbamoyl-2-methyl)propyl or 2-(1-dimethylcarbamoyl-3-methyl)butyl.

Naphthyl-lower alkoxy is, for example, naphthyl-$C_1$–$C_4$alkoxy, such as naphthylmethoxy, 2-naphthylethoxy, 3-naphthylpropyloxy or 4-naphthylbutyloxy.

Naphthyl-lower alkyl is, for example, naphthyl-$C_1$–$C_4$alkyl, such as naphthylmethyl, 2-naphthylethyl, 3-naphthylpropyl or 4-naphthylbutyl.

Lower alkoxy is, for example, $C_1$–$C_7$alkoxy, preferably $C_1$–$C_5$alkoxy, such as methoxy, ethoxy, propyloxy, isopropyloxy, butyloxy, isobutyloxy, sec-butyloxy, tert-butyloxy, pentyloxy or a hexyloxy or heptyloxy group.

Lower alkanoylamino-lower alkoxy is, for example, $C_1$–$C_7$alkanoylamino-$C_2$–$C_4$alkoxy, such as 2-formylaminoethoxy, 2-acetylaminoethoxy, 2-propionylaminoethoxy, 2-butyrylaminoethoxy, 2-isobutyrylaminoethoxy, 2-pivaloylaminoethoxy, 3-formylaminopropyloxy, 3-acetylaminopropyloxy, 3-propionylaminopropyloxy, 3-butyrylaminopropyloxy, 3-isobutyrylaminopropyloxy or 3-pivaloylaminopropyloxy.

Lower alkanoylamino-lower alkyl is, for example, $C_1$–$C_7$alkanoylamino-$C_2$–$C_4$alkyl, such as 2-formylaminoethyl, 2-acetylaminoethyl, 2-propionylaminoethyl, 2-butyrylaminoethyl, 2-isobutyrylaminoethyl, 2-pivaloylaminoethyl, 3-formylaminopropyl, 3-acetylaminopropyl, 3-propionylaminopropyl, 3-butyrylaminopropyl, 3-isobutyrylaminopropyl or 3-pivaloylaminopropyl.

Lower alkanoyl-lower alkoxy (oxo-lower alkoxy) carries the lower alkanoyl group in a position higher than the α-position and is, for example, $C_1$–$C_7$alkanoyl-$C_1$–$C_4$alkoxy, such as 4-acetylbutoxy.

Lower alkanoyloxy is, for example, $C_1$–$C_7$alkanoyloxy, such as formyloxy, acetyloxy, propionyloxy, butyryloxy, isobutyryloxy or pivaloyloxy.

Lower alkanoyloxy-lower alkyl carries the lower alkanoyloxy group in a position higher than the α-position and is, for example, $C_1$–$C_7$alkanoyloxy-$C_1$–$C_4$alkyl, such as 4-acetoxybutyl.

Lower alkanesulfonyl-(hydroxy)-lower alkoxy is, for example, $C_1$–$C_7$alkanesulfonyl-$C_1$–$C_4$-(hydroxy)alkoxy, such as 3-methanesulfonyl-2-hydroxy-propyloxy.

Lower alkanesulfonylamino-lower alkoxy is, for example, $C_1$–$C_7$alkanesulfonylamino-$C_2$–$C_4$-alkoxy, such as 2-methanesulfonylaminoethoxy, 3-methanesulfonylaminopropyloxy or 4-methanesulfonylaminobutyloxy.

Lower alkanesulfonylamino-lower alkyl is, for example, $C_1$–$C_7$alkanesulfonylamino-$C_1$–$C_4$-alkyl, such as ethanesulfonylaminomethyl, 2-ethanesulfonylaminoethyl, 3-ethanesulfonylaminopropyl or 3-(1,1-dimethylethanesulfonylamino)propyl.

Lower alkanesulfonylamino-lower alkyl is, for example, $C_1$–$C_7$alkanesulfonylamino-$C_2$–$C_4$-alkyl, such as 2-ethanesulfonylaminoethyl, 3-ethanesulfonylaminopropyl or 4-methanesulfonylaminobutyl.

Lower alkanesulfonyl-lower alkoxy is, for example, $C_1$–$C_7$alkanesulfonyl-$C_1$–$C_4$alkoxy, such as methanesulfonylmethoxy or 3-methanesulfonyl-2-hydroxy-propyloxy.

Lower alkanesulfonyl-lower alkyl is, for example, $C_1$–$C_7$alkanesulfonyl-$C_1$–$C_4$alkyl, such as ethanesulfonylmethyl, 2-ethanesulfonylethyl, 3-ethanesulfonylpropyl or 3-(1,1-dimethylethanesulfonyl)propyl.

Lower alkenyl is, for example, $C_1$–$C_7$alkenyl, such as vinyl or allyl.

Lower alkenyloxy is, for example, $C_1$–$C_7$alkenyloxy, such as allyloxy.

Lower alkenyloxycarbonyl is, for example, $C_1$–$C_7$alkenyloxycarbonyl, such as vinyloxycarbonyl or allyloxycarbonyl.

Lower alkenyloxy-lower alkoxy is, for example, $C_1$–$C_7$alkenyloxy-$C_1$–$C_4$alkoxy, such as allyloxymethoxy.

Lower alkenyloxy-lower alkyl is, for example, $C_1$–$C_7$alkenyloxy-$C_1$–$C_4$alkyl, such as allyloxymethyl.

Lower alkoxy is, for example, $C_1$–$C_7$alkoxy, preferably $C_1$–$C_5$alkoxy, such as methoxy, ethoxy, propyloxy, isopropyloxy, butyloxy, isobutyloxy, sec-butyloxy, tert-butyloxy, pentyloxy or a hexyloxy or heptyloxy group.

Lower alkoxycarbonyl is, for example, $C_1$–$C_7$alkoxycarbonyl, preferably $C_1$–$C_5$alkoxycarbonyl, such as methoxycarbonyl, ethoxycarbonyl, propyloxycarbonyl, isopropyloxycarbonyl, butyloxycarbonyl, isobutyloxycarbonyl, sec-butyloxycarbonyl, tert-butyloxycarbonyl, pentyloxycarbonyl or a hexyloxycarbonyl or heptyloxycarbonyl group.

Lower alkoxycarbonylamino-lower alkoxy is, for example, $C_1$–$C_7$alkoxycarbonylamino-$C_2$–$C_7$-alkoxy, preferably $C_2$–$C_5$alkoxycarbonylamino-$C_2$–$C_7$alkoxy, such as methoxycarbonylamino-$C_2$–$C_7$alkoxy, ethoxycarbonylamino-$C_2$–$C_7$alkoxy, propyloxycarbonylamino-$C_2$–$C_7$alkoxy, isopropyloxycarbonylamino-$C_2$–$C_7$alkoxy, butyloxycarbonylamino-$C_2$–$C_7$alkoxy, isobutyloxycarbonylamino-$C_2$–$C_7$alkoxy, sec-butyloxycarbonylamino-$C_2$–$C_7$alkoxy or tert-butyloxycarbonylamino-$C_2$–$C_7$alkoxy, wherein $C_2$–$C_7$alkoxy is, for example, methoxy, ethoxy, propyloxy, butyloxy, pentyloxy or hexyloxy.

Lower alkoxycarbonylamino-lower alkyl is, for example, $C_1$–$C_7$alkoxycarbonylamino-$C_2$–$C_7$-alkyl, preferably $C_2$–$C_5$alkoxycarbonylamino-$C_2$–$C_7$alkyl, such as methoxycarbonylamino-$C_2$–$C_7$alkyl, ethoxycarbonylamino-$C_2$–$C_7$alkyl, propyloxycarbonylamino-$C_2$–$C_7$alkyl, isopropyloxycarbonylamino-$C_2$–$C_7$alkyl, butyloxycarbonylamino-$C_2$–$C_7$alkyl, isobutyloxycarbonylamino-$C_2$–$C_7$alkyl, sec-butyloxycarbonylamino-$C_2$–$C_7$alkyl or tert-butyloxycarbonylamino-$C_2$–$C_7$alkyl, wherein $C_2$–$C_7$alkyl is, for example, methyl, ethyl, propyl, butyl, pentyl or hexyl.

Lower alkoxycarbonyl-lower alkoxy is, for example, $C_1$–$C_4$alkoxycarbonyl-$C_1$–$C_4$alkoxy, such as methoxycarbonyl- or ethoxycarbonyl-methoxy, 2-methoxycarbonyl- or 2-ethoxycarbonyl-ethoxy, 2- or 3-methoxycarbonyl- or 2- or 3-ethoxycarbonyl-propyloxy- or 4-methoxycarbonyl- or 4-ethoxycarbonyl-butyloxy, especially methoxycarbonyl- or ethoxycarbonyl-methoxy or 3-methoxycarbonyl- or 3-ethoxycarbonyl-propyloxy.

Lower alkoxycarbonyl-lower alkyl is, for example, $C_1$–$C_4$alkoxycarbonyl-$C_1$–$C_4$alkyl, such as methoxycarbonyl- or ethoxycarbonyl-methyl, 2-methoxycarbonyl- or 2-ethoxycarbonyl-ethyl, 3-methoxycarbonyl- or 3-ethoxycarbonyl-propyl or 4-ethoxycarbonylbutyl.

Lower alkoxyimino-lower alkyl is, for example, N-($C_1$–$C_4$alkoxy)imino-$C_2$–$C_4$alkyl, such as 3-methoxyiminopropyl.

Lower alkoxy-lower alkenyl is, for example, $C_1$–$C_4$alkoxy-$C_2$–$C_4$alkenyl, such as 4-methoxybut-2-enyl.

Lower alkoxy-lower alkenyloxy is, for example, $C_1$–$C_4$alkoxy-$C_2$–$C_4$alkenyloxy, such as 4-methoxybut-2-enyloxy.

Lower alkoxy-lower alkoxy is, for example, $C_1$–$C_4$alkoxy-$C_2$–$C_4$alkoxy, such as 2-methoxy-, 2-ethoxy- or 2-propyloxy-ethoxy, 3-methoxy- or 3-ethoxy-propyloxy or 4-methoxybutyloxy, especially 3-methoxypropyloxy or 4-methoxybutyloxy.

Lower alkoxy-lower alkoxy-lower alkyl is, for example, $C_1$–$C_4$alkoxy-$C_1$–$C_4$alkoxy-$C_1$–$C_4$alkyl, such as 2-methoxy-, 2-ethoxy- or 2-propyloxy-ethoxymethyl, 2-(2-methoxy-, 2-ethoxy- or 2-propyloxy-ethoxy)ethyl, 3-(3-methoxy- or 3-ethoxy-propyloxy)propyl or 4-(2-methoxybutyloxy)butyl, especially 2-(3-methoxypropyloxy)ethyl or 2-(4-methoxybutyloxy)ethyl.

Lower alkoxy-lower alkyl is, for example, $C_1$–$C_4$alkoxy-$C_1$–$C_4$alkyl, such as ethoxymethyl, propyloxymethyl, butyloxymethyl, 2-methoxy-, 2-ethoxy- or 2-propyloxy-ethyl, 3-methoxy- or 3-ethoxy-propyl or 4-methoxybutyl, especially 3-methoxypropyl or 4-methoxybutyl.

Lower alkyl may be straight-chained or branched and/or bridged and is, for example, corresponding $C_1$–$C_7$alkyl, such as methyl, ethyl, propyl, isopropyl, butyl, isobutyl, sec-butyl, tert-butyl, or a pentyl, hexyl or heptyl group. Lower alkyl $R_2$ or $R_3$ is especially $C_2$–$C_7$alkyl, lower alkyl $R_5$ or $R_7$ is especially branched $C_3$–$C_7$alkyl and lower alkyl $R_8$ or $R_3$ is, for example, straight-chained, branched or bridged $C_3$–$C_7$alkyl.

Lower alkylamino is, for example, $C_1$–$C_4$alkylamino, such as methylamino, ethylamino, propylamino, butylamino, isobutylamino, sec-butylamino or tert-butylamino.

Lower alkylamino-lower alkoxy is, for example, $C_1$–$C_4$alkylamino-$C_1$–$C_4$alkoxy, such as propylaminomethoxy, 2-methylamino-, 2-ethylamino-, 2-propylamino- or 2-butylaminoethoxy, 3-ethylamino- or 3-propylamino-propyloxy or 4-methylaminobutoxy.

Lower alkylamino-lower alkyl is, for example, $C_1$–$C_4$alkylamino-$C_1$–$C_4$alkyl, such as propylaminomethyl, 2-methylamino-, 2-ethylamino-, 2-propylamino- or 2-butylamino-ethyl, 3-ethylamino- or 3-propylamino-propyl or 4-methylaminobutyl.

Lower alkylcarbamoyl-lower alkoxy is, for example, N—$C_1$–$C_7$alkylcarbamoyl-$C_1$–$C_4$alkoxy, such as methyl- or dimethyl-carbamoyl-$C_1$–$C_4$alkoxy, e.g. methylcarbamoylmethoxy, 2-methylcarbamoylethoxy or 3-methylcarbamoylpropyloxy.

Lower alkylcarbamoyl-lower alkoxy is, for example, N—$C_1$–$C_7$alkylcarbamoyl-$C_1$–$C_4$alkyl, such as methyl- or dimethyl-carbamoyl-$C_1$–$C_4$alkyl, e.g. methylcarbamoylmethyl, 2-methylcarbamoylethyl or 3-methylcarbamoylpropyl.

Lower alkylene the free valencies of which originate from carbon atoms that are adjacent to one another or in the 1,3-, 1,4- or 1,5-position relative to one another is, for example, 1,3-propylene, 1,2-ethylene or 1,3-, 2,3- or 1,4-butylene or 1,3-, 2,3-, 2,4- or 1,5-butylene.

Lower alkylthio-(hydroxy)-lower alkoxy is, for example, N—$C_1$–$C_4$alkylthio-$C_1$–$C_4$(hydroxy)-alkoxy, such as 2-hydroxy-3-methylthiopropyloxy.

Lower alkylthio is, for example, $C_1$–$C_7$alkylthio, preferably $C_1$–$C_5$alkylthio, such as methylthio, ethylthio, propylthio, isopropylthio, butylthio, isobutylthio, sec-butylthio, tert-butylthio, pentylthio or a hexylthio or heptylthio group.

Lower alkylthio-lower alkoxy is, for example, N—$C_1$–$C_4$alkylthio-$C_1$–$C_4$alkoxy, such as methylthio-$C_1$–$C_4$alkoxy, e.g. methylthiomethoxy, 2-methylthioethoxy or 3-methylthiopropyloxy.

Lower alkylthio-lower alkoxy is, for example, N—$C_1$–$C_4$alkylthio-$C_1$–$C_4$alkoxy, such as methylthio-$C_1$–$C_4$alkoxy, e.g. methylthiomethoxy, 2-methylthioethoxy or 3-methylthiopropyloxy.

Lower alkylthio-lower alkyl is, for example, N—$C_1$–$C_4$alkylthio-$C_1$–$C_4$alkyl, such as methylthio-$C_1$–$C_4$alkyl, e.g. methylthiomethyl, 2-methylthioethyl or 3-methylthiopropyl.

Oxo-lower alkoxy is, for example, oxo-$C_1$–$C_4$alkoxy, such as 3,3-dimethyl-2-oxo-butyloxy.

Phenyl-lower alkoxycarbonyl is, for example, phenyl-$C_1$–$C_4$alkoxycarbonyl, such as benzyloxycarbonyl, 1- or 2-phenylethoxycarbonyl, 3-phenylpropyloxycarbonyl or 4-phenylbutyloxycarbonyl.

Phenyl-lower alkoxycarbonyloxy is, for example, phenyl-$C_1$–$C_4$alkoxycarbonyloxy, such as benzyloxycarbonyloxy, 1- or 2-phenylethoxycarbonyloxy, 3-phenylpropyloxycarbonyloxy or 4-phenylbutyloxycarbonyloxy.

Phenyl-lower alkoxy-lower alkoxy is, for example, phenyl-$C_1$–$C_4$alkoxy-$C_2$–$C_4$alkoxy, such as 2-benzyloxyethoxy, 1- or 2-phenylethoxyethoxy, 3-benzyloxypropyloxy, 2-phenylpropyloxyethoxy, 3-phenylpropyloxypropyloxy or 4-benzyloxybutyloxy.

Phenyl-lower alkyl is, for example, phenyl-$C_1$–$C_4$alkyl, such as benzyl, 1- or 2-phenylethyl, 3-phenylpropyl or 4-phenylbutyl.

Naphthyl-lower alkyl is, for example, naphthyl-$C_1$–$C_4$alkyl, such as benzyl, 1- or 2-naphthylethyl, 3-naphthylpropyl or 4-naphthylbutyl.

Piperidino-lower alkoxy is, for example, piperidino-$C_1$–$C_4$alkoxy, such as piperidinomethoxy, 2-pipeddinoethoxy or 3-piperidinopropyloxy.

Piperidino-lower alkyl is, for example, piperidino-$C_1$–$C_4$alkyl, such as piperidinomethyl, 2-piperidinoethyl or 3-piperidinopropyl.

Polyhalo-lower alkanesulfonylamino-lower alkoxy is, for example, trifluoro-$C_1$–$C_7$alkanesulfonyl-$C_1$–$C_4$alkoxy, such as trifluoromethanesulfonylaminobutyloxy.

Polyhalo-lower alkanesulfonylamino-lower alkyl is, for example, trifluoro-$C_1$–$C_7$alkanesulfonyl-$C_1$–$C_4$alkyl, such as trifluoromethanesulfonylaminobutyl.

Polyhalo-lower alkoxy is, for example, tri-halo-$C_1$–$C_4$alkoxy, such as trifluoromethoxy or 2,2,2-trichloroethoxy.

Polyhalo-lower alkyl is, for example, tri-halo-$C_1$–$C_4$alkyl, such as trifluoromethyl or 2,2,2-trichloroethyl.

Pyridyl-lower alkoxy-lower alkoxy is, for example, pyridyl-$C_1$–$C_4$alkoxy-$C_2$–$C_4$alkoxy, such as 2-pyridylmethoxyethoxy, 1- or 2-pyridylethoxyethoxy, 3-pyridylmethoxypropyloxy, 2-pyridylpropyloxyethoxy, 3-pyridylpropyloxypropyloxy or 4-pyridylmethoxybutyloxy.

Pyridyl-lower alkoxy, which may also be partially hydrogenated or N-oxidised, is, for example, pyridyl-$C_1$–$C_4$alkoxy, tetrahydropyridyl-$C_1$–$C_4$alkoxy or N-oxidopyridyl-$C_1$–$C_4$alkoxy, such as pyridylmethoxy, tetrahydropyridylmethoxy, N-oxidopyridylmethoxy, 1- or 2-pyridylethoxy, 3-pydriylpropyloxy, 2-pyridylpropyloxy, 3-pyridylpropyloxy or 4-pyridylbutyloxy.

Pyridyl-lower alkyl is, for example, pyridyl-$C_1$–$C_4$alkyl, such as pyridylmethyl, 1- or 2-pyridylethyl, 3-pyridylpropyl or 4-pyridylbutyl.

Pyrimidinyl-lower alkyl is, for example, pyrimidyl-$C_1$–$C_4$alkyl, such as pyrimidylmethyl, 1- or 2-pyrimidylethyl, 3-pyrimidylpropyl or 4-pyrimidylbutyl.

Quinolinyl-lower alkyl is, for example, quinolinyl-$C_1$–$C_4$alkyl, such as quinolinylmethyl, 1- or 2-quinolinylethyl, 3-quinolinylpropyl or 4-quinolinylbutyl.

Pyrimidinylthio-lower alkoxy is, for example, pyrimidylthio-$C_1$–$C_4$alkoxy, such as pyrimidylthiomethoxy, 1- or 2-pyrimidylthioethoxy, 3-pyrimidylthiopropyloxy or 4-pyrimidylthiobutyloxy.

Pyrimidinylthio-lower alkyl is, for example, pyrimidylthio-$C_1$–$C_4$alkyl, such as pyrimidylthiomethyl, 1- or 2-pyrimidylthioethyl, 3-pyrimidylthiopropyl or 4-pyrimidylthiobutyl.

Pyrrolidino-lower alkoxy is, for example, pyrrolidino-$C_2$–$C_4$alkoxy, such as 2-pyrrolidinoethoxy or 3-pyrrolidinopropyloxy.

Pyrrolidino-lower alkyl is, for example, pyrrolidino-$C_1$–$C_4$alkyl, such as pyrrolidinomethyl, 2-pyrrolidinoethyl or 3-pyrrolidinopropyl.

S,S-Dioxothiomorpholino-lower alkoxy is, for example, S,S-dioxothiomorpholino-$C_1$–$C_4$alkoxy, such as S,S-dioxothiomorpholinomethoxy or 2-(S,S-dioxo)-thiomorpholinomethoxy.

S,S-Dioxothiomorpholino-lower alkyl is, for example, S,S-dioxothiomorpholino-$C_1$–$C_4$alkyl, such as S,S-dioxothiomorpholinomethyl or 2-(S,S-dioxo)-thiomorpholinomethyl.

S-Oxothiomorpholino-lower alkoxy is, for example, S-oxothiomorpholino-$C_1$–$C_4$alkoxy, such as S-oxothiomorpholinomethoxy or 2-(S-oxo)-thiomorpholinomethoxy.

S-Oxothiomorpholino-lower alkyl is, for example, S-oxothiomorpholino-$C_1$–$C_4$alkyl, such as S-oxothiomorpholinomethyl or 2-(S-oxo)-thiomorpholinoethyl.

Thiazolinylthio-lower alkoxy is, for example, thiazolinylthio-$C_1$–$C_4$alkoxy, such as thiazolinylthiomethoxy, 1- or 2-thiazolinylthioethoxy, 3-thiazolinylthiopropyloxy or 4-thiazolinylthiobutyloxy.

Thiazolinylthio-lower alkyl is, for example, thiazolinylthio-$C_1$–$C_4$alkyl, such as thiazolinylthiomethyl, 1- or 2-thiazolinylthioethyl, 3-thiazolinylthiopropyl or 4-thiazolinylthiobutyl.

Thiazolyl-lower alkoxy is, for example, thiazolyl-$C_1$–$C_4$alkoxy, such as thiazolylmethoxy, 1- or 2-thiazolylethoxy, 3-thiazolylpropyloxy or 4-thiazolylbutyloxy.

Thienyl-lower alkoxy-lower alkoxy is, for example, thienyl-$C_1$–$C_4$alkoxy-$C_2$–$C_4$alkoxy, such as 2-thienylmethoxyethoxy, 1- or 2-thienylethoxyethoxy, 3-thienylmethoxypropyloxy, 2-thienylpropyloxyethoxy, 3-thienylpropyloxypropyloxy or 4-thienylmethoxybutyloxy.

Thienyl-lower alkyl is, for example, thienyl-$C_1$–$C_4$alkyl, such as thienylmethyl, 1- or 2-thienylethyl, 3-thienylpropyl or 4-thienylbutyl.

Tri-halo-lower alkanoyloxy is, for example, trifluoroacetyloxy.

Tri-lower alkylsilyloxy is, for example, trimethylsilyloxy, dimethyl(butyl)silyloxy or tributylsilyloxy.

Salts of compounds having salt-forming groups are especially acid addition salts, salts with bases or, where several salt-forming groups are present, can also be mixed salts or internal salts.

Such salts are formed, for example, by compounds of formula I having an acid group, for example a carboxy group, and are, for example, salts thereof with suitable bases, such as non-toxic metal salts derived from metals of groups I, Ib, IIa and IIb of the Periodic Table of the Elements, for example alkali metal salts, especially lithium, sodium or potassium salts, or alkaline earth metal salts, for example magnesium or calcium salts, also zinc salts or ammonium salts, as well as salts formed with organic amines, such as unsubstituted or hydroxy-substituted mono-, di- or tri-alkylamines, especially mono-, di- or tri-lower alkylamines, or with quaternary ammonium bases, for example with methyl-, ethyl-, diethyl- or triethyl-amine, mono-, bis- or tris-(2-hydroxy-lower alkyl)amines, such as ethanol-, diethanol- or triethanol-amine, tris (hydroxymethyl)methylamine or 2-hydroxy-tert-butylamine, N,N-di-lower alkyl-N-(hydroxy-lower alkyl)-amine, such as N,N-dimethyl-N-(2-hydroxyethyl)-amine, or N-methyl-D-glucamine, or quaternary ammonium hydroxides, such as tetrabutylammonium hydroxide.

The compounds of formula I having a basic group, for example an amino group, can form acid addition salts, for example with suitable inorganic acids, for example hydrohalic acids, such as hydrochloric acid or hydrobromic acid, or sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic, sulfo or phosphonic acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2acetoxybenzoic acid, embonic acid, nicotinic acid or isonicotinic acid, as well as with amino acids, such as the α-amino acids mentioned hereinbefore, and with methanesulfonic acid, ethanesulfonic acid, 2-hydroxyethanesulfonic acid, ethane-1,2-disulfonic add, benzenesulfonic acid, 4-methylbenzenesulfonic acid, naphthalene-2-sulfonic acid, 2- or 3-phosphoglycerate, glucose-6-phosphate, or N-cyclohexylsulfamic acid (forming cyclamates) or with other acidic organic compounds, such as ascorbic acid. Compounds of formula I having acid and basic groups can also form internal salts.

For isolation and purification purposes it is also possible to use pharmaceutically unacceptable salts.

The compounds of formula I are valuable intermediates in the preparation of medicinal active ingredients, for example of compounds of formula II

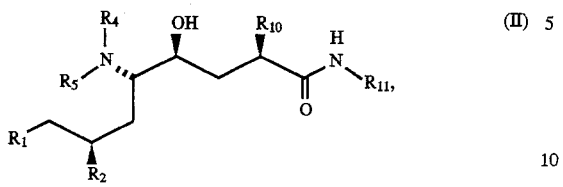

wherein $R_1$ is an aliphatic, cycloaliphatic, cycloaliphatic-aliphatic, aromatic or heteroaromatic radical, a hydroxy group that is aliphatically, araliphatically or heteroarylaliphatically etherified or protected by a hydroxy-protecting group, or an aliphatically etherified mercapto group, and $R_2$ is an aliphatic, cycloaliphatic, cycloaliphatic-aliphatic, araliphatic or heteroarylaliphatic radical, or $R_1$ and $R_2$ together are a divalent aliphatic radical, $R_4$ is hydrogen, lower alkyl or lower alkanoyl, $R_5$ is hydrogen or, if $R_4$ is lower alkyl, may also be lower alkyl, $R_{10}$ is an aliphatic, cycloaliphatic, cycloaliphatic-aliphatic or araliphatic radical, and $R_{11}$ is an aliphatic, cycloaliphatic or heteroaromatic-aliphatic radical, and the salts thereof, which can be used, for example, as antihypertensives.

The compounds of formula I are especially valuable intermediates for δ-amino-γ-hydroxy-ω-aryl-alkanoic acid amides of formula II wherein $R_1$ is an aliphatic, cycloaliphatic, cycloaliphatic-aliphatic, aromatic or heteroaromatic radical, a hydroxy group that is aliphatically, araliphatically or heteroarylaliphatically etherified or protected by a hydroxy-protecting group, or an aliphatically etherified mercapto group, and $R_2$ is an aliphatic, cycloaliphatic, cycloaliphatic-aliphatic, araliphatic or heteroarylaliphatic radical, or $R_1$ and $R_2$ together form a divalent aliphatic radical, $R_4$ is hydrogen, an aliphatic or araliphatic radical or an amino-protecting group, and $R_5$ is hydrogen or an aliphatic radical, $R_{10}$ is lower alkyl, lower alkenyl, cycloalkyl or aryl-lower alkyl, and $R_{11}$ is lower alkyl, cycloalkyl, free or aliphatically esterified or etherified hydroxy-lower alkyl; amino-lower alkyl that is unsubstituted or N-lower alkanoylated, N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl or a heteroaryl radical that is bonded via a carbon atom and optionally hydrogenated and/or oxo-substituted or lower alkyl substituted by a heteroaryl radical that is bonded via a carbon atom and optionally hydrogenated and/or oxo-substituted, and the salts thereof, which are effective as renin inhibitors and can therefore be used as antihypertensives.

The compounds of formula I are especially suitable for the preparation of compounds of formula IIa

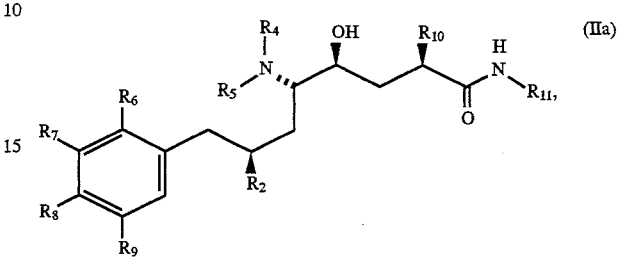

wherein $R_2$ is lower alkyl, 3- to 8-membered cycloalkyl, 3- to 8-membered cycloalkyl-lower alkyl, or a phenyl-lower alkyl, naphthyl-lower alkyl, furyl-lower alkyl, thienyl-lower alkyl, optionally partially hydrogenated or N-oxidised pyridyl-lower alkyl, pyrimidinyl-lower alkyl or quinolinyl-lower alkyl radical that is unsubstituted or substituted in the phenyl, naphthyl or heteroaryl moiety by lower alkyl, lower alkoxy, halogen and/or by trifluoromethyl, $R_4$ is hydrogen, lower alkyl or lower alkanoyl, especially hydrogen, $R_5$ is hydrogen or, when $R_4$ is lower alkyl, is hydrogen or lower alkyl, and $R_6$, $R_7$, $R_8$ and $R_9$ are as defined under formula Ia, $R_{10}$ is lower alkyl, lower alkenyl, cycloalkyl or aryl-lower alkyl, and $R_{11}$ is lower alkyl, cycloalkyl, free or aliphatically esterified or etherified hydroxy-lower alkyl; amino-lower alkyl that is unsubstituted or N-lower alkanoylated, N-mono- or N,N-di-lower alkylated or N,N-disubstituted by lower alkylene, by hydroxy-, lower alkoxy- or lower alkanoyloxy-lower alkylene, by unsubstituted or N'-lower alkanoylated or N'-lower alkylated aza-lower alkylene, by oxa-lower alkylene or by optionally S-oxidised thia-lower alkylene; free or esterified or amidated carboxy-lower alkyl, free or esterified or amidated dicarboxy-lower alkyl, free or esterified or amidated carboxy-(hydroxy)-lower alkyl, free or esterified or amidated carboxycycloalkyl-lower alkyl, cyano-lower alkyl, lower alkanesulfonyl-lower alkyl, unsubstituted or N-mono- or N,N-di-lower alkylated thiocarbamoyl-lower alkyl, unsubstituted or N-mono- or N,N-di-lower alkylated sulfamoyl-lower alkyl or a heteroaryl radical that is bonded via a carbon atom and optionally hydrogenated and/or oxo-substituted or lower alkyl substituted by a heteroaryl radical that is bonded via a carbon atom and optionally hydrogenated and/or oxo-substituted, and wherein preferably $R_2$ is branched $C_1$–$C_4$alkyl, such as isopropyl, or 3- to 5-membered cycloalkyl-$C_1$–$C_4$alkyl, such as cyclopropylmethyl, $R_4$ is hydrogen, $C_1$–$C_4$alkyl, such as methyl, or $C_1$–$C_4$alkanoyl, such as acetyl, especially hydrogen, $R_5$ is hydrogen or, when $R_4$ is $C_1$–$C_4$alkyl, is hydrogen or $C_1$–$C_4$alkyl, such as methyl, $R_6$ is hydrogen, $R_7$ is $C_1$–$C_4$alkyl, such as methyl or tert-butyl, $C_1$–$C_4$alkoxy-$C_1$–$C_4$alkyl, such as 3-methoxypropyl, $C_1$–$C_4$alkoxy-$C_1$–$C_4$alkoxy, such as 3-methoxypropyloxy, $C_1$–$C_4$alkoxy-$C_1$–$C_4$alkoxy-$C_1$–$C_4$alkyl, such as 3-methoxybutyl, phenyl-$C_1$–$C_4$alkyl, such as benzyloxy, pyridyl-$C_1$–$C_4$-alkoxy, such as pyridylmethoxy, $C_1$–$C_4$alkylthio-$C_1$–$C_4$alkoxy, such as 3-methylthiopropyloxy, $C_1$–$C_4$alkanesulfonyl-$C_1$–$C_4$alkoxy, such as 3-methanesulfonylpropyloxy, $C_1$–$C_4$alkanoyloxy-$C_1C_4$alkoxy, such as 3-acetoxypropyloxy, $C_1C_4$alkoxycarbonyl-$C_1$–$C_4$alkoxy, such as methoxy- or ethoxy-carbonylmethoxy, carbamoyl-$C_1$–$C_4$alkoxy, such as carbamoylmethoxy, or di-$C_1$–$C_4$alkylcarbamoyl-$C_1$–$C_4$alkoxy, such as dimethylcarbamoylmethoxy, $R_8$ is hydrogen, $C_1$–$C_4$alkyl, such as methyl or tert-butyl, hydroxy or $C_1$–$C_4$alkoxy, such as methoxy, or together with $R_9$ is $C_1$–$C_4$alkylenedioxy, such as methylenedioxy or ethylenedioxy, $R_9$ is hydrogen or together with $R_8$ is $C_1$–$C_4$alkylenedioxy, such as methylenedioxy or ethylenedioxy, $R_{10}$ is branched $C_1$–$C_4$alkyl, such as isopropyl, and $R_{11}$ is carbamoyl-$C_1$–$C_4$alkyl, such as 2- or 3-carbamoylpropyl, 2-(3-carbamoyl)propyl or 1-(2-carbamoyl-2-methyl)propyl, N—$C_1$–$C_4$alkylcarbamoyl-$C_1$–$C_4$alkyl, such as 3-(N-methylcarbamoyl)propyl, 2-[1-(N-methylcarbamoyl)]propyl, 1-[2-(N-methylcarbamoyl)]propyl, especially 1-[2(R)-(N-methylcarbamoyl)]propyl, N,N-di-$C_1$–$C_4$alkylcarbamoyl-$C_1$–$C_4$alkyl, such as N,N-dimethylcarbamoylmethyl or 2-(N,N-dimethylcarbamoyl)ethyl, 3-(N,N-dimethylcarbamoyl)propyl, morpholino-$C_1$–$C_4$alkyl, such as 2-morpholinoethyl, 3-morpholinopropyl or 1-(2-morpholino-2-methyl)propyl, thiomorpholino-$C_1$–$C_4$alkyl, such as 2-thiomorpholinoethyl, 4-(1-$C_1$–$C_4$alkanoylpiperidyl)-$C_1$–$C_4$alkyl, such as 2-[4-(1-acetyl)piperidinyl]ethyl, 2-oxopyrrolidinyl-$C_1$–$C_4$alkyl, such as 2-oxopyrrolidin-5(S)-ylmethyl or 2-oxopyrrolidin-5(R)-ylmethyl, and the salts thereof.

The compounds of formula I are suitable above all for the preparation of compounds of formula IIa wherein $R_2$ is branched $C_1$–$C_4$alkyl, such as isopropyl, $R_4$, $R_5$, $R_6$ and $R_9$ are hydrogen, $R_7$ is $C_1$–$C_4$alkoxy-$C_1$–$C_4$alkoxy, such as 3-methoxypropyloxy, or $C_1$–$C_4$alkoxy-$C_1$–$C_4$alkyl, such as 3-methoxybutyl, $R_8$ is $C_1$–$C_4$alkyl, such as isopropyl or tert-butyl, or $C_1$–$C_4$alkoxy, such as methoxy, $R_{10}$ is branched $C_1$–$C_4$alkyl, such as isopropyl, and $R_{11}$ is carbamoyl-$C_1$–$C_4$alkyl, such as 2- or 3-carbamoylpropyl, 2-(3-carbamoyl)propyl or 1-(2-carbamoyl-2-methyl)propyl, N—$C_1$–$C_4$alkylcarbamoyl-$C_1$–$C_4$alkyl, such as 3-(N-methylcarbamoyl)propyl, 2-[1-(N-methylcarbamoyl)]propyl, 1-[2-(N-methylcarbamoyl)]propyl, especially 1-[2(R)-(N-methylcarbamoyl)]propyl, N,N-di-$C_1$–$C_4$alkylcarbamoyl-$C_1$–$C_4$alkyl, such as N,N-dimethylcarbamoylmethyl or 2-(N,N-dimethylcarbamoyl)ethyl, 3-(N,N-dimethylcarbamoyl)propyl, morpholino-$C_1$–$C_4$alkyl, such as 2-morpholinoethyl, 3-morpholinopropyl or 1-(2-morpholino-2-methyl)propyl, thiomorpholino-$C_1$–$C_4$alkyl, such as 2-thiomorpholinoethyl, 4-(1-$C_1$–$C_4$alkanoylpiperidyl)-$C_1$–$C_4$alkyl, such as 2-[4-(1-acetyl)piperidinyl]ethyl, 2-oxopyrrolidinyl-$C_1$–$C_4$alkyl, such as 2-oxopyrrolidin-5(S)-ylmethyl or 2-oxopyrrolidin-5(R)-ylmethyl, and the salts thereof.

Intermediates of formula I are converted into renin inhibitors of formula II in customary manner, for example as follows: in a compound of formula I wherein $R_1$ is formyl, free or esterified carboxy or hydroxymethyl, $R_4$ is an amino-protecting group and $R_5$ is hydrogen, the free or esterified carboxy group that may be present is reduced to formyl in customary manner, for example with dibutylaluminium hydride in toluene, or a hydroxymethyl group that may be present is oxidised to formyl in customary manner, for example with pyridine/sulfur trioxide in dimethyl sulfoxide/dichloromethane, the corresponding aldehyde of formula I wherein $R_3$ is formyl is reacted in an ethereal solvent, such as tetrahydrofuran, and, if necessary, in the presence of an activator, such as 1,2-dibromobutane, with magnesium and a compound of formula

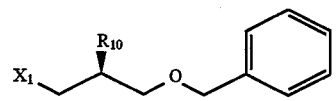

wherein $X_1$ is halogen, such as bromine, the resulting compound of formula IV

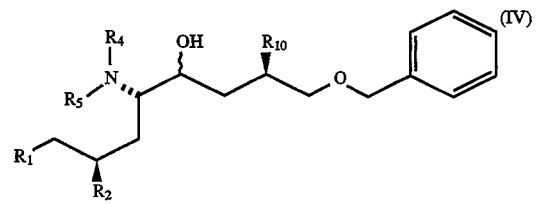

is temporarily protected at the amino and hydroxy groups by a divalent protecting group $X_2$, such as isopropylidene, for example by reaction under acid conditions, such as in the presence of p-toluenesulfonic acid monohydrate, with an acetone ketal, such as an acetone di-lower alkyl ketal, for example with 2,2-dimethoxpropane, the resulting diastereoisomeric mixture is separated into its components in customary manner, for example by flash column chromatography on silica gel using ethyl acetate/hexane (1:2) as eluant, and the benzyl group is removed from the diastereoisomer of formula V

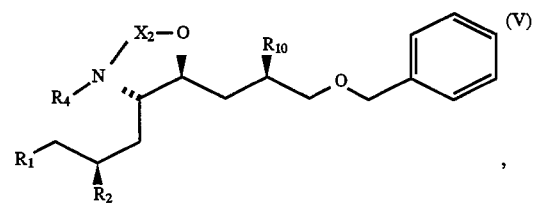

in customary manner, for example by catalytic hydrogenation in the presence of palladium on carbon, the terminal hydroxymethyl group thus freed is oxidised to formyl in customary manner, for example by reaction with a perruthenate, for example with tetrapropylammonium perruthenate in the presence of N-methylmorpholine-N-oxide, the formyl group thus formed is oxidised to carboxy in customary manner, for example with a permanganate, such as potassium permanganate, the resulting acid of formula VI

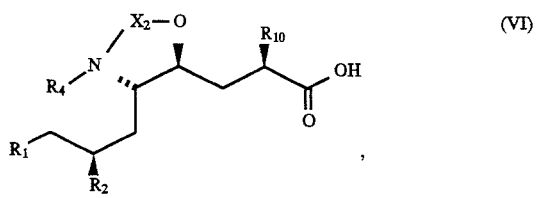

is condensed in customary manner, for example in the presence of a cyanophosphonic acid ester, such as cyanophosphonic acid diethyl ester, and a tertiary organic amine, such as triethylamine, preferably in N,N-dimethylformamide, with an amine of formula VII

and the protecting groups are removed from the resulting compound of formula VIII

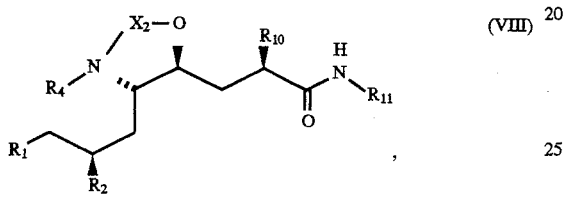

in customary manner, for example by treatment with an acid, for example with hydrochloric acid in a cyclic ether, such as dioxane, and, if desired, a compound obtainable by the process is converted into a different compound of formula II, a mixture of isomers which may be obtainable is separated and/or a compound of formula II having at least one salt-forming group obtainable by the process is converted into a salt or a salt obtainable by the process is converted into the free compound or into a different salt.

The invention relates especially to compounds of formula I wherein $R_1$ is lower alkyl; lower alkenyl; 3- to 8-membered cycloalkyl; 3- to 8-membered cycloalkyl-lower alkyl; a phenyl or naphthyl radical that is unsubstituted or mono-, di- or tri-substituted by amino-lower alkoxy, amino-lower alkyl, aryl-lower alkoxy, carbamoyl-lower alkoxy, carbamoyl-lower alkyl, carboxy-lower alkoxy, carboxy-lower alkoxy, carboxy-lower alkyl, cyano-lower alkoxy, cyano-lower alkyl, 3- to 8-membered cycloalkoxy, 3- to 8-membered cycloalkoxy-lower alkoxy, 3- to 8-membered cycloalkoxy-lower alkyl, 3- to 8-membered cycloalkyl, di-lower alkylamino, di-lower alkylamino-lower alkoxy, di-lower alkylamino-lower alkyl, pyridyl-lower alkoxy, tetrahydropyridyl-lower alkoxy, N-oxidopyridyl-lower alkoxy, thiazolyl-lower alkoxy, morpholino-lower alkoxy, pyridylthio-lower alkoxy, N-oxidopyridylthio-lower alkoxy, pyridylthio-lower alkyl, N-oxidopyridylthio-lower alkyl, halo-(hydroxy)-lower alkoxy, halogen, hydroxy, hydroxy-lower alkoxy, hydroxy-lower alkyl, imidazolylthio-lower alkoxy, imidazolylthio-lower alkyl, morpholino-lower alkoxy, morpholino-lower alkyl, N-mono- or N,N-di-lower alkylcarbamoyl-lower alkoxy, N-mono- or N,N-di-lower alkylcarbamoyl-lower alkyl, optionally N-oxidised pyridyl-lower alkyl, N'-lower alkylpiperazino- or N'-lower alkanoylpiperazino-lower alkoxy, N'-lower alkylpiperazino- or N'-lower alkanoylpiperazino-lower alkyl, naphthyl, naphthyl-lower alkoxy, lower alkanoylamino-lower alkoxy, lower alkanoylamino-lower alkyl, lower alkanoyl-lower alkoxy, lower alkanoyloxy-lower alkyl, lower alkanesulfonyl-(hydroxy)-lower alkoxy, lower alkanesulfonylamino-lower alkoxy, lower alkanesulfonylamino-lower alkyl, lower alkanesulfonyl-lower alkoxy, lower alkanesulfonyl-lower alkyl, lower alkenyloxy, lower alkenyloxy-lower alkoxy, lower alkenyloxy-lower alkyl, lower alkoxy, lower alkoxycarbonylamino-lower alkoxy, lower alkoxycarbonylamino-lower alkyl, lower alkoxycarbonyl-lower alkoxy, lower alkoxycarbonyl-lower alkyl, lower alkoxyimino-lower alkyl, lower alkoxy-lower alkenyl, lower alkoxy-lower alkenyloxy, lower alkoxy-lower alkoxy, lower alkoxy-lower alkoxy-lower alkyl, lower alkoxy-lower alkyl, lower alkyl, lower alkylamino, lower alkylamino-lower alkoxy, lower alkylamino-lower alkyl, lower alkylthio-(hydroxy)-lower alkoxy, lower alkylthio-lower alkoxy, lower alkylthio-lower alkoxy, lower alkylthio-lower alkyl, oxo-lower alkoxy, piperazino-lower alkoxy, piperazino-lower alkyl, piperidino-lower alkoxy, piperidino-lower alkyl, polyhalo-lower alkanesulfonylamino-lower alkoxy, polyhalo-lower alkanesulfonylamino-lower alkyl, polyhalo-lower alkoxy, polyhalo-lower alkyl, pyrimidinylthio-lower alkoxy, pyrimidinylthio-lower alkoxy, pyrimidinylthio-lower alkyl, pyrrolidino-lower alkoxy, pyrrolidino-lower alkyl, S,S-dioxothiomorpholino-lower alkoxy, S,S-dioxothiomorpholino-lower alkyl, S-oxothiomorpholino-lower alkoxy, S-oxothiomorpholino-lower alkyl, thiazolylthio-lower alkoxy, thiazolinylthio-lower alkoxy, thiazolylthio-lower alkyl, thiazolinylthio-lower alkyl and/or by thiomorpholino; or a phenyl radical that is disubstituted by a fused-on benzo or cyclohexanol ring; an unsubstituted or lower alkyl-, lower alkoxy-, halo- and/or trifluoromethyl-substituted furyl, thienyl, pyridyl, pyrimidinyl, indolyl or quinolinyl radical; lower alkoxy; lower alkenyloxy; phenyl-lower alkoxy that is unsubstituted or substituted in the phenyl moiety by lower alkyl, lower alkoxy, halogen and/or by trifluoromethyl; or a furyl-lower alkoxy, thienyl-lower alkoxy, pyridyl-lower alkoxy or quinolinyl-lower alkoxy group that is unsubstituted or substituted in the ring by lower alkyl, lower alkoxy, halogen and/or by trifluoromethyl; lower alkanoyloxy; tri-halo-lower alkanoyloxy; a benzoyloxy or phenyl-lower alkoxycarbonyloxy group that is unsubstituted or substituted by lower alkyl, lower alkoxy, halogen, trifluoromethyl and/or by nitro; tri-lower alkylsilyloxy; benzyl(di-lower alkyl)silyloxy; or lower alkylthio, and $R_2$ is lower alkyl, 3- to 8-membered cycloalkyl, 3- to 8-membered cycloalkyl-lower alkyl, or a phenyl-lower alkyl, naphthyl-lower alkyl, furyl-lower alkyl, thienyl-lower alkyl, optionally partially hydrogenated or N-oxidised pyridyl-lower alkyl, pyrimidinyl-lower alkyl or quinolinyl-lower alkyl radical that is unsubstituted or substituted in the phenyl, naphthyl or heteroaryl moiety by lower alkyl, lower alkoxy, halogen and/or by trifluoromethyl, or $R_1$ and $R_2$ together are lower alkylene the free valencies of which originate from carbon atoms that are adjacent to one another or in the 1,3-, 1,4- or 1,5-position relative to one another, $R_3$ is carboxy, lower alkoxycarbonyl, lower alkenyloxycarbonyl or an unsubstituted or lower alkyl-, lower alkoxy-, halo- and/or trifluoromethyl-substituted phenyl-lower alkoxycarbonyl or phenyloxycarbonyl radical, $R_4$, is hydrogen, lower alkyl, an unsubstituted or lower alkyl-, lower alkoxy-, halo- and/or trifluoromethyl-substituted phenyl- or naphthyl-lower alkyl radical, lower alkanoyl, tri-halo-lower alkanoyl, an unsubstituted or lower alkyl-, lower alkoxy-, halo-, trifluoromethyl- and/or nitro-substituted benzoyl or phenyl-lower alkoxycarbonyl group, tri-lower alkylsilyl or benzyl-(di-lower alkyl)silyl, and $R_5$ is hydrogen or lower alkyl, and the salts thereof.

The invention relates above all to compounds of formula Ib

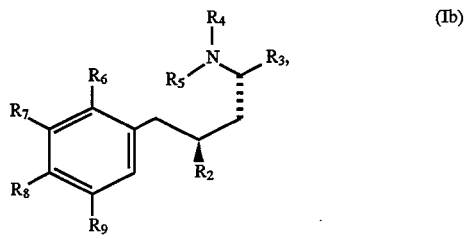

wherein $R_2$ is lower alkyl, 3- to 8-membered cycloalkyl, 3- to 8-membered cycloalkyl-lower alkyl, or a phenyl-lower alkyl, naphthyl-lower alkyl, furyl-lower alkyl, thienyl-lower alkyl, optionally partially hydrogenated or N-oxidised pyridyl-lower alkyl, pyrimidinyl-lower alkyl or quinolinyl-lower alkyl radical that is unsubstituted or substituted in the phenyl, naphthyl or heteroaryl moiety by lower alkyl, lower alkoxy, halogen and/or by trifluoromethyl, $R_3$ is carboxy, lower alkoxycarbonyl, lower alkenyloxycarbonyl or an unsubstituted or lower alkyl-, lower alkoxy-, halo- and/or trifluoromethyl-substituted phenyl-lower alkoxycarbonyl or phenyloxycarbonyl radical, $R_4$ is hydrogen, lower alkyl, an unsubstituted or lower alkyl-, lower alkoxy-, halo- and/or trifluoromethyl-substituted phenyl- or naphthyl-lower alkyl radical, lower alkanoyl, tri-halo-lower alkanoyl, an unsubstituted or lower alkyl-, lower alkoxy-, halo-, trifluoromethyl- and/or nitro-substituted benzoyl or phenyl-lower alkoxycarbonyl group, tri-lower alkylsilyl or benzyl-(di-lower alkyl)silyl, $R_5$ is hydrogen or lower alkyl, $R_6$ is hydrogen, hydroxy, lower alkoxy, cycloalkoxy, lower alkoxy-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, $R_7$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoyl-amino-lower alkyl, lower alkoxycarbonylamino-lower alkyl, lower alkoxyimino-lower alkyl, amino-lower alkoxy, lower alkylamino-lower alkoxy, di-lower alkylamino-lower alkoxy, lower alkanoylamino-lower alkoxy, lower alkoxycarbonylamino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl lower alkoxy, carbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R_8$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolylthio-lower alkyl or thiazolinylthio-lower alkyl, imidazolylthio-lower alkyl, optionally N-oxidised pyridylthio-lower alkyl, pyrimidinylthio-lower alkyl, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl, cyano-lower alkyl, carboxy-lower alkyl, lower alkoxycarbonyl-lower alkyl, carbamoyl-lower alkyl, N-mono- or N,N-di-lower alkylcarbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-, di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino-lower alkoxy, cyano-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, or together with $R_9$ is lower alkylenedioxy or a fused-on benzo or cyclohexanol ring, $R_9$ together with $R_8$ is lower alkylenedioxy or a fused-on benzo or cyclohexeno ring, or is hydrogen, lower alkyl, hydroxy, lower alkoxy or cycloalkoxy, and the salts thereof.

The invention relates especially to compounds of formula Ib wherein $R_2$ is lower alkyl, 3- to 5-membered cycloalkyl-lower alkyl or cycloalkyl, $R_3$ is carboxy, lower alkoxycarbonyl, formyl or hydroxymethyl, $R_4$ is lower alkoxycarbonyl or unsubstituted or lower alkyl-, lower alkoxy-, nitro- and/or halo-substituted α-phenyl-lower alkoxycarbonyl, $R_5$ and $R_6$ are hydrogen, $R_7$ is lower alkyl, lower alkoxy-lower alkyl, lower alkoxy-lower alkoxy, lower alkoxy-lower alkoxy-lower alkyl, unsubstituted or lower alkyl-, lower alkoxy-, hydroxy-, halo-, nitro- and/or amino-substituted phenyl-lower alkoxy, optionally N-oxidised pyridyl-lower alkoxy, lower alkylthio-lower alkoxy, lower alkanesulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R_8$ is hydrogen, lower alkyl, hydroxy, lower alkoxy or polyhalo-lower alkoxy or together with $R_9$ is lower alkylenedioxy, and $R_9$ is hydrogen or together with $R_8$ is lower alkylenedioxy, and the salts thereof.

The invention relates preferably to compounds of formula Ib wherein $R_2$ is branched $C_1$–$C_4$alkyl, such as isopropyl, or 3- to 5-membered cycloalkyl-$C_1$–$C_4$alkyl, such as cyclopropylmethyl, $R_3$ is carboxy, $C_1$–$C_4$alkoxycarbonyl, formyl or hydroxymethyl, $R_4$ is $C_1$–$C_4$alkoxycarbonyl, such as tert-butyloxycarbonyl, or αphenyl-$C_1$–$C_4$alkoxycarbonyl, such as benzyloxycarbonyl, $R_5$ and $R_5$ are hydrogen, $R_7$ is $C_1$–$C_4$alkyl, such as methyl or tert-butyl, $C_1$–$C_4$alkoxy-$C_1$–$C_4$alkyl, $C_1$–$C_4$alkoxy-$C_1$–$C_4$alkyl, such as 3-methoxypropyloxy, $C_1$–$C_4$alkoxy-$C_1$–$C_4$alkoxy-$C_1$–$C_4$alkyl, such as 3-methoxybutyl, phenyl-$C_1$–$C_4$alkoxy, such as benzyloxy, pyridyl-$C_1$–$C_4$alkoxy, such as pyridylmethoxy, $C_1$–$C_4$alkylthio-$C_1$–$C_4$alkoxy, such as 3-methylthiopropyloxy, $C_1$–$C_4$alkanesulfonyl-$C_1$–$C_4$-alkoxy, such as 3-methanesulfonylpropyloxy, $C_1$–$C_4$alkanoyl-$C_1$–$C_4$alkoxy, such as Acetoxymethoxy, $C_1$–$C_4$alkoxycarbonyl-$C_1$–$C_4$alkoxy, such as methoxy- or ethoxy-carbonylmethoxy, carbamoyl-$C_1$–$C_4$alkoxy, such as carbamoylmethoxy, or di-$C_1$–$C_4$alkylcarbamoyl-$C_1$–$C_4$alkoxy, such as dimethylcarbamoylmethoxy, $R_8$ is hydrogen, $C_1$–$C_4$alkyl, such as methyl or tert-butyl, hydroxy or $C_1$–$C_4$alkoxy, such as methoxy, or together with $R_9$ is $C_1$–$C_4$alkylenedioxy, and $R_9$ is hydrogen or together with $R_8$ is $C_1$–$C_4$alkylenedioxy, and the salts thereof, The invention relates very especially to compounds of formula Ib wherein $R_2$ is branched $C_1$–$C_4$alkyl, such as isopropyl, $R_3$ is carboxy, formyl or hydroxymethyl, $R_4$ is $C_1$–$C_4$alkoxycarbonyl, $R_5$, $R_6$ and $R_9$ are hydrogen, $R_7$ is $C_1$–$C_4$alkoxy-$C_1$–$C_4$alkoxy, such as 3-methoxypropyloxy, or $C_1$–$C_4$alkoxy-$C_1$–$C_4$alkyl, such as 3-methoxybutyl, and $R_8$ is hydrogen, $C_1$–$C_4$alkyl, such as isopropyl or tert-butyl, or $C_1$–$C_4$alkoxy, such as methoxy, and the salts thereof.

The invention relates specifically to the compounds of formula I mentioned in the Examples and to the salts thereof, especially to the salts thereof, The process for the preparation of compounds of formula I comprises hydrolysing a compound of formula IX

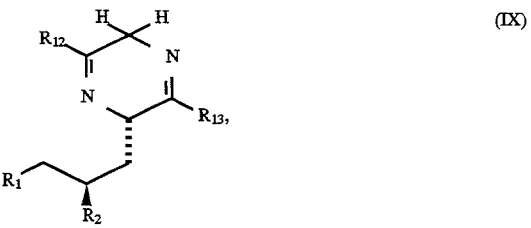

wherein $R_{12}$ and $R_{13}$ are each independently of the other aliphatically, araliphatically or aromatically etherified hydroxy, especially lower alkoxy, and $R_1$ and $R_2$ are as defined above under formula I, with opening of the pyrazine ring to form the corresponding compound of formula I wherein $R_3$ is aliphatically, araliphatically or aromatically esterified carboxy of the formula —C(=O)—$R_{13}$, and, if desired, converting a-compound obtainable by the process into a different compound of formula I, separating any mixtures of isomers which may be obtainable and/or converting a compound of formula I having at least one salt-forming group obtainable by the process into a salt or converting a salt obtainable by the process into the free compound or into a different salt.

The starting materials of formula IX can be prepared, for example, by reacting a compound of formula X

with a compound of formula

wherein X is reactive esterified hydroxy, for example halogen, such as chlorine, or a group of the formula —O—C(=O)—$CH_2$—$R_2$, metallating the resulting compound of formula XII

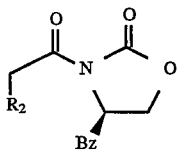

by reaction with a metal base, such as lithium hexamethyldisilazide in a cyclic ether, such as tetrahydrofuran, preferably with cooling at approximately from −80° C. to −60° C., preferably at approximately −70° C., and then condensing the product with a compound of formula XIII

wherein $X_1$ is reactive esterified hydroxy, especially halogen, such as bromine; in the resulting compound of formula XIV

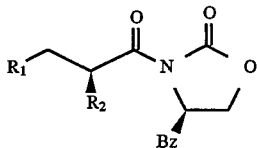

hydrolysing the 4-benzyl-2-oxo-oxazolidin-1-ylcarbonyl group selectively to carboxy, for example with lithium hydroxide/hydrogen peroxide, reducing the carboxy group to hydroxymethyl, for example with sodium borohydride/iodine in tetrahydrofuran, halogenating the hydroxymethyl group, for example with N-bromosuccinimide/triphenylphosphine in dichloromethane, and condensing the reaction product of formula XV

wherein $X_2$ is reactive esterified hydroxy, especially halogen, for example bromine, with a metal salt of a compound of formula XVI

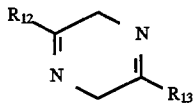

obtainable from that compound by treatment with a metal base, for example with butyllithium in hexane with cooling at approximately from −80° C. to −60° C., preferably at approximately −70° C.

In analogous manner, compounds of formula I wherein $R_1$ and $R_2$ together form a divalent aliphatic radical, especially lower alkylene, are obtained by condensing the starting material of formula X not with a compound of formula XI but with a compound of formula XVII

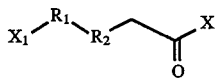

wherein X is reactive esterified hydroxy, for example halogen, such as chlorine, or a group of the formula O—(C=O)—CH$_2$—R$_2$—R$_1$—X$_1$; in the reaction product of formula XVIII

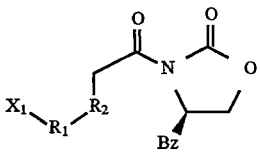

hydrolysing the 4-benzyl-2-oxo-oxazolidin-1-ylcarbonyl group selectively to carboxy, reducing the carboxy group to hydroxymethyl, halogenating the hydroxymethyl group and reacting the reaction product of formula XIX

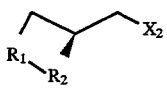

with a metal salt of a compound of formula XVI.

Compounds of formula I obtainable in accordance with the invention can, as mentioned, be converted into different compounds of formula I.

For example, in compounds of formula I wherein $R_3$ is esterified carboxy, the esterified carboxy group can be converted into carboxy in customary manner, for example by basic or acid hydrolysis. Conversely, carboxy $R_3$ can be esterified in customary manner, for example by reaction with an alcohol in the presence of an acidic agent, or by conversion into chlorocarbonyl and further reaction with an alcohol in the presence of a basic condensation agent.

It is also possible to reduce compounds of formula I wherein $R_3$ is free or esterified carboxy in customary manner, for example with dibutylaluminium hydride in toluene, or by conversion into the corresponding acid chloride, for example by reaction with oxalyl chloride, and subsequent reduction, for example with sodium tri-tert-butyloxyaluminium hydride in tetrahydrofuran, to the corresponding aldehyde wherein $R_1$ is formyl.

Furthermore, in resulting compounds of formula I wherein $R_4$ and $R_5$ are hydrogen, an amino-protecting group or an aliphatic or araliphatic radical $R_4$ and, if desired, an aliphatic radical $R_5$ can be introduced in customary manner. For example, a primary amine can be N-mono- or N,N-di-lower alkylated, N-aralkylated or N-lower alkanoylated by reaction with an alkylating agent, an arylalkylating agent or an alkanoylating agent in the presence of a basic condensation agent. In analogous manner it is also possible to introduce an amino-protecting group; for example tert-butyloxycarbonyl can be introduced by reaction with di-tert-butyl dicarbonate in the presence of a tri-lower alkylamine, such as N,N-diisopropyl-N-ethylamine.

In compounds of formula I wherein the radical $R_1$ is a group of formula Ia, it is also possible to replace hydroxy $R_6$, $R_2$, $R_8$ and/or $R_9$ by one of the etherified hydroxy groups mentioned under formula I or II by reacting the corresponding compound of formula I, II, VI, VIa or VII wherein $R_6$, $R_2$, $R_8$ and/or $R_9$ is hydroxy in customary manner, for example in the presence of a basic condensation agent, with a compound of the formula(e) R'$_6$—Y, R'$_7$—Y, R'$_8$—Y and/or R'$_9$—Y wherein $R_6$ is lower alkyl or free or esterified or amidated carboxy-lower alkyl, R'$_7$ is lower alkyl, lower alkoxy-lower alkyl, lower alkoxy-lower alkoxy-lower alkyl, cycloalkoxy-lower alkyl, optionally lower alkanoylated, halogenated or sulfonylated hydroxy-lower alkyl, oxo-lower alkyl, lower alkyl, lower alkenyl, cycloalkoxy-lower alkyl, lower alkoxy-lower alkyl, lower alkoxy-lower alkenyl, lower alkenyloxy-lower alkyl, lower alkenyloxy-lower alkyl, lower alkanoyl-lower alkyl, optionally S-oxidised lower alkylthio-lower alkyl, lower alkylthio-(hydroxy)-lower alkyl, aryl-lower alkyl, optionally hydrogenated heteroaryl-lower alkyl, optionally hydrogenated heteroarylthio-lower alkyl, cyano-lower alkyl or free or esterified or amidated carboxy-lower alkyl, R'$_8$ is lower alkyl, lower alkoxy-lower alkyl, hydroxy-lower alkyl, aryl-lower alkyl, halogenated lower alkyl, cyano-lower alkyl or free or esterified or amidated carboxy-lower alkyl, and R'$_9$ is lower alkyl, and Y is reactive esterified hydroxy, especially hydroxy groups esterified by a mineral acid, by sulfuric acid or by an organic sulfonic acid, such as halogen, preferably chlorine, bromine or iodine, groups of the formula O—SO$_2$—O—R'$_A$, or lower alkanesulfonyloxy or unsubstituted or substituted benzenesulfonyloxy, especially methane-, ethane-, benzene-, p-toluene- or p-bromobenzene-sulfonyloxy. The reaction is, as mentioned, preferably carded out in the presence of a basic condensation agent, such as an alkali metal carbonate, for example potassium carbonate, in an inert solvent, such as a lower alkanol, such as methanol, ethanol, butanol, tert-butanol or especially amyl alcohol, advantageously at elevated temperature, for example in a temperature range of approximately from 40° to 140° C., if necessary with removal of the resulting water of reaction by distillation, for example by azeotropic distillation.

It is also possible for salts of compounds of formula I obtainable in accordance with the process to be converted in a manner known per se into the free compounds, for example by treatment with a base, such as an alkali metal hydroxide, a metal carbonate or metal hydrogen carbonate, or ammonia, or another of the salt-forming bases mentioned at the beginning, or with an acid, such as a mineral acid, for example with hydrochloric acid, or another of the salt-forming acids mentioned at the beginning.

Resulting salts can be converted into different salts in a manner known per se: acid addition salts, for example, by treatment with a suitable metal salt, such as a sodium, barium or silver salt, of a different acid in a suitable solvent in which an inorganic salt being formed is insoluble and is therefore eliminated from the reaction equilibrium, and basic salts by freeing of the free acid and conversion into a salt again.

The compounds of formula I, including their salts, may also be obtained in the form of hydrates or may include the solvent used for crystallisation.

As a result of the close relationship between the novel compounds in free form and in the form of their salts, hereinabove and hereinbelow any reference to the free compounds and their salts is to be understood as including also the corresponding salts and free compounds, respectively, as appropriate and expedient.

The invention relates also to those forms of the process in which a compound obtainable as intermediate at any stage is used as starting material and the remaining steps are carried out or the process is interrupted at any stage or a starting material is formed under the reaction conditions or is used in the form of a reactive derivative or salt, or a compound obtainable in accordance with the process of the invention is formed under the process conditions and further processed in situ. It is preferable to use those starting materials which result in the compounds described above as being very preferred or very especially preferred.

The invention relates also to novel starting materials, which have been developed specifically for the preparation of the compounds according to the invention, especially the group of starting materials resulting in the compounds of formula I described at the beginning as being preferred, to processes for their preparation and to their use as intermediates.

This relates especially to compounds of formula IX which, as mentioned, are suitable as intermediates in the preparation of compounds of formula I.

The invention relates accordingly also to compounds of formula IX

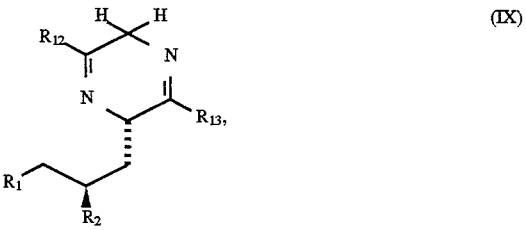

wherein

R$_1$ is an aliphatic, cycloaliphatic, cycloaliphatic-aliphatic, aromatic or heteroaromatic radical, a hydroxy group that is aliphatically, araliphatically or heteroarylaliphatically etherified or protected by a hydroxy-protecting group, or an aliphatically etherified mercapto group, and R$_2$ is an aliphatic, cycloaliphatic, cycloaliphatic-aliphatic, araliphatic or heteroarylaliphatic radical, or R$_1$ and R$_2$ together form a divalent aliphatic radical, and R$_{12}$ and R$_{13}$ are each independently of the other aliphatically, araliphatically or aromatically etherified hydroxy, and to the salts thereof and to processes for the preparation thereof.

The invention relates especially to compounds of formula IX wherein

R$_1$ is lower alkyl; lower alkenyl; 3- to 8-membered cycloalkyl; 3- to 8-membered cycloalkyl-lower alkyl; a phenyl or naphthyl radical that is unsubstituted or mono-, di- or tri-substituted by amino-lower alkoxy, amino-lower alkyl, aryl-lower alkoxy, carbamoyl-lower alkoxy, carbamoyl-lower alkyl, carboxy-lower alkoxy, carboxy-lower alkoxy, carboxy-lower alkyl, cyano-lower alkoxy, cyano-lower alkyl, 3- to 8-membered cycloalkoxy, 3- to 8-membered cycloalkoxy-lower alkoxy, 3- to 8-membered cycloalkoxy-lower alkyl, 3- to 8-membered cycloalkyl, di-lower alkylamino, di-lower alkylamino-lower alkoxy, di-lower alkylamino-lower alkyl, pyridyl-lower alkoxy, tetrahydropyridyl-lower alkoxy, N-oxidopyridyl-lower alkoxy, thiazolyl-lower alkoxy, morpholino-lower alkoxy, pyridylthio-lower alkoxy, N-oxidopyridylthio-lower alkoxy, pyridylthio-lower alkyl, N-oxidopyridylthio-lower alkyl, halo-(hydroxy) -lower alkoxy, halogen, hydroxy, hydroxy-lower alkoxy, hydroxy-lower alkyl, imidazolylthio-lower alkoxy, imidazolylthio-lower alkyl, morpholino-lower alkoxy, morpholino-lower alkyl, N-mono- or N,N-di-lower alkylcarbamoyl-lower alkoxy, N-mono- or N,N-di-lower alkylcarbamoyl-lower alkyl, optionally N-oxidised pyridyl-lower alkyl, N'-lower alkylpiperazino- or N'-lower alkanoylpiperazino-lower alkoxy, N'-lower alkylpiperazino- or N'-lower alkanoylpiperazino-lower alkyl, naphthyl, naphthyl-lower alkoxy, lower alkanoylamino-lower alkoxy, lower alkanoylamino-lower alkyl, lower alkanoyl-lower alkoxy, lower alkanoyloxy-lower alkyl, lower alkanesulfonyl-(hydroxy)-lower alkoxy, lower alkanesulfonylamino-lower alkoxy, lower alkanesulfonylamino-lower alkyl, lower alkanesulfonyl-lower alkoxy, lower alkanesulfonyl-lower alkyl, lower alkenyloxy, lower alkenyloxy-lower alkoxy, lower alkenyloxy-lower alkyl, lower alkoxy, lower alkoxycarbonylamino-lower alkoxy, lower alkoxycarbonylamino-lower alkyl, lower alkoxycarbonyl-lower alkoxy, lower alkoxycarbonyl-lower alkyl, lower alkoxyimino-lower alkyl, lower alkoxy-lower alkenyl, lower alkoxy-lower alkenyloxy, lower alkoxy-lower alkoxy, lower alkoxy-lower alkoxy-lower alkyl, lower alkoxy-lower alkyl, lower alkyl, lower alkylamino, lower alkylamino-lower alkoxy, lower alkylamino-lower alkyl, lower alkylthio-(hydroxy)-lower alkoxy, lower alkylthio-lower alkoxy, lower alkylthio-lower alkoxy, lower alkylthio-lower alkyl, oxo-lower alkoxy, piperazino-lower alkoxy, piperazino-lower alkyl, piperidino-lower alkoxy, piperidino-lower alkyl, polyhalo-lower alkanesulfonylamino-lower alkoxy, polyhalo-lower alkanesulfonylamino-lower alkyl, polyhalo-lower alkoxy, polyhalo-lower alkyl, pyrimidinylthio-lower alkoxy, pyrimidinylthio-lower alkoxy, pyrimidinylthio-lower alkyl, pyrrolidino-lower alkoxy, pyrrolidino-lower alkyl, S,S-dioxothiomorpholino-lower alkoxy, S,S-dioxothiomorpholino-lower alkyl, S-oxothiomorpholino-lower alkoxy, S-oxomorpholino-lower alkyl, thiazolylthio-lower alkoxy, thiazolinylthio-lower alkoxy, thiazolylthio-lower alkyl, thiazolinylthio-lower alkyl and/or by thiomorpholino; or a phenyl radical disubstituted by a fused-on benzo or cyclohexeno ring; an unsubstituted or lower alkyl-, lower alkoxy-, halo- and/or trifluoromethyl-substituted furyl, thienyl, pyridyl, pyrimidinyl, indolyl or quinolinyl radical; lower alkoxy; lower alkenyloxy; phenyl-lower alkoxy that is unsubstituted or substituted in the phenyl moiety by lower alkyl, lower alkoxy, halogen and/or by trifluoromethyl; furyl-lower alkoxy, thienyl-lower alkoxy, pyridyl-lower alkoxy or quinolinyl-lower alkoxy groups that are unsubstituted or substituted in the ring by lower alkyl, lower alkoxy, halogen and/or by trifluoromethyl; lower alkanoyloxy; tri-halo-lower alkanoyloxy; an unsubstituted or lower alkyl-, lower alkoxy-, halo-, trifluoromethyl- and/or nitro-substituted benzoyloxy or phenyl-lower alkoxycarbonyloxy group; tri-lower alkylsilyloxy; benzyl(di-lower alkyl)silyloxy; or lower alkylthio, R$_2$ is lower alkyl, 3- to 8-membered cycloalkyl, 3- to 8-membered cycloalkyl-lower alkyl, or a phenyl-lower alkyl, naphthyl-lower alkyl, phrnyl-lower alkyl, thienyl-lower alkyl, optionally partially hydrogenated or N-oxidised pyridyl-lower alkyl, pyrimidinyl-lower alkyl or quinolinyl-lower alkyl radical that is unsubstituted or substituted in the phenyl, naphthyl or heteroaryl moiety by lower alkyl, lower alkoxy, halogen and/or by trifluoromethyl, or R$_1$ and R$_2$ together are lower alkylene the free valencies of which originate from carbon atoms that are adjacent to one another or in the 1,3-, 1,4- or 1,5-position relative to one another, and R$_{12}$ and R$_{13}$ are each independently of the other lower alkoxy, lower alkenyloxy, unsubstituted or lower alkyl-, lower alkoxy-, halo- and/or trifluoromethyl-substituted phenyloxy, or phenyl-lower alkoxy or naphthyl-lower alkoxy that is unsubstituted or substituted in the phenyl or naphthyl moiety by lower alkyl, lower alkoxy, halogen and/or by trifluoromethyl, and the salts thereof.

The invention relates especially to compounds of formula IXa

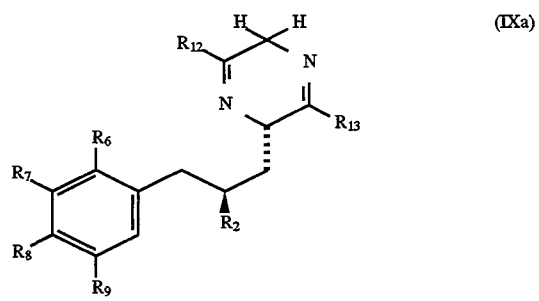

wherein

R$_2$ is lower alkyl, 3- to 8-membered cycloalkyl, 3- to 8-membered cycloalkyl-lower alkyl, or a phenyl-lower alkyl, naphthyl-lower alkyl, furyl-lower alkyl, thienyl-lower alkyl, optionally partially hydrogenated or N-oxidised pyridyl-lower alkyl, pyrimidinyl-lower alkyl or quinolinyl-lower alkyl radical that is unsubstituted or substituted in the phenyl, naphthyl or heteroaryl moiety by lower alkyl, lower alkoxy, halogen and/or by trifluoromethyl, R$_6$ is hydrogen, hydroxy, lower alkoxy, cycloalkoxy, lower alkoxy-lower alkoxy, carboxy-lower alkoxy, lower alkoxycarbonyl-lower alkoxy, cabamoyl-lower alkoxy or N-mono- or N,N-di-lower alkylcarbamoyl-lower alkoxy, R$_7$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoyl-amino-lower alkyl, lower alkoxycarbonylamino-lower alkyl, lower alkoxyimino-lower alkyl, amino-lower alkoxy, lower alkylamino-lower alkoxy, di-lower alkylamino-lower alkoxy, lower alkanoylamino-lower alkoxy, lower alkoxycarbonylamino-lower alkoxy, oxo-lower alkoxy lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, carbamoyl-lower alkoxy, N-mono- or N,N-di-lower alkylcarbamoyl-lower alkoxy, carbon-lower alkyl, lower alkoxycarbonyl-lower alkyl, carbamoyl-lower alkyl or N-mono- or N,N-di-lower alkylcarbamoyl-lower alkyl, R$_8$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolylthio-lower alkyl or thiazolinylthio-lower alkyl, imidazolylthio-lower alkoxy, optionally N-oxidised pyridylthio-lower alkyl, pyrimidinylthio-lower alkyl, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino- lower alkyl, cyano-lower alkyl, carboxy-lower alkyl, lower alkoxycarbonyl-lower alkyl, carbamoyl-lower alkyl, N-mono- or N,N-di-lower alkylcarbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-, di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio- lower alkoxy, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino- lower alkoxy, cyano-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy or together with $R_9$ is lower alkylenedioxy or a fused-on benzo or cyclohexeno ring, $R_9$ together with $R_8$ is lower alkylenedioxy or a fused-on benzo or cyclohexeno ring, or is hydrogen, lower alkyl, hydroxy, lower alkoxy or cycloalkoxy, and $R_{12}$ and $R_{13}$ are each independently of the other lower alkoxy, lower alkenyloxy, unsubstituted or lower alkyl-, lower alkoxy-, halo- and/or trifluoromethyl- substituted phenyloxy, or phenyl-lower alkoxy or naphthyl-lower alkoxy that is unsubstituted or substituted in the phenyl or naphthyl moiety by lower alkyl, lower alkoxy, halogen and/or by trifluoromethyl, and the salts thereof.

The invention relates especially to compounds of formula IXa wherein $R_2$ is lower alkyl, 3- to 5-membered cycloalkyl-lower alkyl or cycloalkyl, $R_6$ is hydrogen, $R_7$ is lower alkyl, lower alkoxy-lower alkyl, lower alkoxy-lower alkoxy, lower alkoxy-lower alkoxy-lower alkyl, unsubstituted or lower alkyl-, lower alkoxy-, hydroxy-, halo-, nitro- and/or amino-substituted phenyl-lower alkoxy, optionally N-oxidised pyridyl-lower alkoxy, lower alkylthio-lower alkoxy, lower alkanesulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R_8$ is hydrogen, lower alkyl, hydroxy, lower alkoxy or polyhalo-lower alkoxy or together with $R_9$ is lower alkylenedioxy, $R_9$ is hydrogen or together with $R_5$ is lower alkylenedioxy, and $R_{12}$ and $R_{13}$ are each independently of the other lower alkoxy, lower alkenyloxy, unsubstituted or lower alkyl-, lower alkoxy-, halo- and/or trifluoromethyl- substituted phenyloxy, or phenyl-lower alkoxy that is unsubstituted or substituted in the phenyl moiety by lower alkyl, lower alkoxy, halogen and/or by trifluoromethyl, and the salts thereof.

The invention relates above all to compounds of formula IXa wherein $R_2$ is branched $C_1$–$C_4$alkyl, such as isopropyl, or 3- to 5-membered cycloalkyl-$C_1$–$C_4$alkyl, such as cyclopropylmethyl, $R_6$ is hydrogen, $R_7$ is alkyl, such as methyl or tert-butyl, $C_1$–$C_4$alkoxy-$C_1$–$C_4$alkyl, such as 3-methoxypropyl, $C_1$–$C_4$alkoxy-$C_1$–$C_4$alkoxy, such as 3-methoxypropyloxy, $C_1$–$C_4$alkoxy-$C_1$–$C_4$alkoxy-$C_1$–$C_4$alkyl, such as 3-methoxybutyl, phenyl-$C_1$–$C_4$alkoxy, such as benzyloxy, pyridyl-$C_1$–$C_4$alkoxy, such as pyridylmethoxy, $C_1$–$C_4$alkylthio-$C_1$–$C_4$alkoxy, such as 3-methylthiopropyloxy, $C_1$–$C_4$alkanesulfonyl-$C_1$–$C_4$alkoxy, such as 3-methanesulfonylpropyloxy, $C_1$–$C_4$alkanoyloxy-$C_1$–$C_4$alkoxy, such as 3-acetoxypropyloxy, $C_1$–$C_4$alkoxycarbonyl-$C_1$–$C_4$alkoxy, such as methoxy- or ethoxy-carbonylmethoxy, carbamoyl-$C_1$–$C_4$alkoxy, such as carbamoylmethoxy, or di-$C_1$–$C_4$alkylcarbamoyl-$C_1$–$C_4$alkoxy, such as dimethylcarbamoylmethoxy, $R_8$ is hydrogen, $C_1$–$C_4$alkyl, such as methyl or tert-butyl, hydroxy or $C_1$–$C_4$alkoxy, such as methoxy, or together with $R_9$ is $C_1$–$C_4$alkylenedioxy, such as methylenedioxy or ethylenedioxy, $R_9$ is hydrogen or together with $R_8$ is $C_1$–$C_4$alkylenedioxy, such as methylenedioxy or ethylenedioxy, and $R_{12}$ and $R_{13}$ are identical or different $C_1$–$C_4$alkoxy or $C_2$–$C_4$alkenyloxy groups, such as methoxy, ethoxy, propyloxy or allyloxy, and the salts thereof.

The invention relates specifically to the compounds of formula IX mentioned in the Examples and to the salts thereof.

The process according to the invention for the preparation of compounds of formula IX comprises condensing a compound of formula

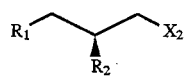 (XV)

wherein $X_2$ is reactive esterified hydroxy, especially halogen, for example bromine, with a metal salt of a compound of formula XVI

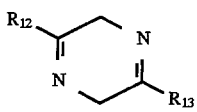

(XVI)

obtainable from that compound by treatment with a metal base and, if desired, converting a compound of formula IX according to the invention into a different compound of formula IX according to the invention, or separating any mixtures of isomers that may be obtainable and/or converting the compound of formula IX obtainable by the process into a salt or converting a salt obtainable by the process into the free compound or into a different salt.

The selective hydrolysis of the 4-benzyl-2-oxo-oxazolidin-1-ylcarbonyl group to carboxy is carried out in customary manner, tot example with lithium hydroxide/hydrogen peroxide.

The reduction of the hydroxymethyl group is carded out in accordance with customary methods, for example with sodium borohydride/iodine in tetrahydrofuran.

The halogenation of the hydroxymethyl group is carried out in accordance with customary methods, for example with N-bromosuccinimide/triphenylphosphine in dichloromethane.

Metal salts of compounds of formula XVI are formed in customary manner by reaction with an alkali metal compound or alkaline earth metal compound of an aliphatic hydrocarbon, preferably with butyllithium in hexane with cooling at approximately from −80° C. to −60° C., preferably at approximately −70° C.

The following Examples serve to illustrate the invention; temperatures are given in degrees Celsius, pressures in mbar.

Mass-spectroscopic measurements are obtained either by conventional MS or in accordance with the "Fast-Atom-Bombardment" (FAB-MS) method. In the former case the mass data relate to the unprotonated molecule ion $(M)^+$ or the protonated molecule ion $(M+H)^+$.

The short names and abbreviations used have the following meanings:

| | |
|---|---|
| $C_{18}$-Nucleosil® | brand name for reversed phase column material for HPLC charged with octadecyl radicals (Nucleosil® $5C_{18}$, Macherey & Nagel, FRG) |
| FAB-MS | Fast-Atom-Bombardment mass spectroscopy |
| FC | flash column chromatography |
| HPLC | high performance liquid chromatography (column dimensions used: 250 × 4.6 mm; stationary phase: Nucleosil® $5C_{18}$; mobile phase: A) water + 0.1% by vol. trifluoroacetic acid B) acetonitrile + 0.1% by vol. trifluoracetic acid; unless otherwise indicated, the following eluant gradient is used: 20–100% B in 20 minutes + 8 minutes 100% B. Eluant gradient (I): linear in 60 minutes from 30% by vol. B + 70% by vol. A to 90% by vol. B + 10% by vol. A |
| Hyflo® | brand name for filter aids (Fluka, Buchs, Switzerland) |
| IR | infrared spectroscopy |
| b.p. | at the pressure indicated in torr |
| ml | milliliters |
| MS | mass spectroscopy |
| $R_f$ | ratio of the migration of a substance to the distance of the eluant front from the starting point in TLC |
| $R_t$ | retention time of a substance in HPLC (in minutes) |
| m.p. | melting point (temperature). |

PREPARATION EXAMPLE 1

2(S)-Amino-4(S)-[4-methoxy-3-(3-methoxypropoxy)-benzyl]-5-methyl-hexanoic acid ethyl ester 1N Hydrochloric acid (3.6 liters, 3.60 mol) is added at room temperature, with stirring, to a solution of the crude product 2(S)-{2(S)-[4-methoxy-3-(3-methoxypropoxy)-benzyl]-3-methylbutyl}-3,6-diethoxy-2,5-dihydro-pyrazine (472 g) in acetonitrile (3.6 liters). After 30 minutes the reaction mixture is carefully poured into an ice-cold saturated aqueous sodium hydrogen carbonate solution. The mixture is extracted with dichloromethane (3×4 liters), and the combined organic phases are washed repeatedly with water and concentrated. After drying in vacuo, the crude title compound is obtained in the form of an oil (351 g): Rf (dichloromethane/methanol/conc. ammonia 850:50:1)= 0.34.

The starting material can be prepared, for example, as follows:

a) 3,6-diethoxy-2,5-dihydro-pyrazine

A solution of triethyloxonium tetrafluoroborate (1.07 kg, 5.36 mol) in dichloromethane (2.5 liters) is added at room temperature, with stirring, to a solution of glycine anhydride (256.7 g, 2.25 mol) in dichloromethane (2.5 liters). The suspension is stirred over a period of 64 hours at room temperature, then cooled to 0° C. and for the purpose of working up a phosphate buffer solution pH 7.36, prepared by dissolving dipotassium hydrogen phosphate (3.29 kg, 4.19 mol) and potassium dihydrogen phosphate (0.945 kg, 1.54 mol) in water (11.2 liters), is added over a period of 5 minutes. The mixture is stirred for a further 30 minutes and then clarified by filtration over Hyflo®. The filtration residue is then washed with dichloromethane (3 liters), the filtrates are combined and the organic phase is removed and the aqueous phase is extracted with dichloromethane (2×2 liters). The combined organic phases are washed with saturated sodium chloride solution (1×2 liters), filtered over cotton wool and the solvent is concentrated. The residue is dissolved in dichloromethane (400 ml); hexane (4 liters) is added, with stirring, and the precipitate that has formed after a further 10 minutes' stirring is filtered off with suction and washed with hexane. The filtrate is concentrated in a rotary evaporator at 40° C. under reduced pressure until crystallisation begins. The resulting suspension is stirred to complete the reaction, with cooling in an ice-bath, and the precipitate is filtered off and washed with a small amount of cold hexane. Drying under a high vacuum at 30° C. yields the pure title compound in the form of a white crystalline solid (230 g). A further 61 g (76% total yield) of title compound are obtained from the mother liquor by further recrystallisation from dichloromethane/hexane. M.p. 82°–83° C. Anal. $C_8H_{14}N_2O_2$ (170.19): calc. C, 56.45; H, 8.29; N, 16.45; found C, 56.42; H, 8.47; N, 16.50.

b) 2(S)-{2(S)-[4-Methoxy-3-(3-methoxypropoxy)-benzyl]-3-methylbutyl}-3-6-diethoxy-2-5-dihydro-pyrazine 1 6M n-butyllithium in hexane (788 ml, 1.26 mol) is added dropwise at −40° C. under an inert atmosphere over a period of 20 minutes to a solution of 3,6-diethoxy-2,5-dihydro-pyrazine (229.8 g, 1.35 mol) in tetrahydrofuran (3.0 liters). The batch is stirred for a further 15 minutes at −40° C. and then a solution of 2(R)-[4-methoxy-3-(3-methoxypropoxy)-benzyl]-3-methyl-butyl bromide (323.4 g, 0.90 mol) in tetrahydrofuran (1.0 liter) is added dropwise thereto over a period of 20 minutes. When the addition is complete, the temperature of the mixture is allowed to rise to −20° C. and the mixture is then stirred at that temperature over a period of 18 hours. The reaction mixture is concentrated and the residue is partitioned between ethyl acetate (1 liter) and water (1 liter). The organic phase is washed with 2×1 liter of water, and the aqueous phases are each back-extracted with 1 liter of ethyl acetate and the combined organic phases are washed with saturated sodium chloride solution (1 liter) and dried over magnesium sulfate. After concentration, the residue is dried under a high vacuum over a period of 1 hour at 35° C. The crude title compound is obtained in admixture with a small amount of epimeric 2(R)-{2(S)-[4-methoxy-3-(3-methoxypropoxy)-benzyl]3-methylbutyl}-3,6-diethoxy-2,5-dihydro-pyrazine (approx. 95:5 diastereoisomeric mixture) and excess 3,6-diethoxy-2,5-dihydro-pyrazine in the form of a colourless oil (472 g): $R_f$ (ethyl acetate/hexane 1:2)=0.20. The 2(R)-[4-methoxy-3-(3-methoxypropoxy)-benzyl]-3-methyl-butyl bromide used as starting material can be prepared, for example, as described below:

a1) 2(R)-[4-Methoxy-3-(3-methoxypropoxy)-benzyl]-3-methyl-butyl bromide

Triphenylphosphine (108.6 g) and, in portions, N-bromosuccinimide (73.7 g) are added in succession at 0° C., with stirring, to a solution of 2(R)-[4-methoxy-3-(3-methoxypropoxy)-benzyl]-3-methyl-butanol (102.2 g) in dichloromethane (2 liters). The batch is stirred for a further 18 hours at room temperature and is then concentrated under reduced pressure. The residue is purified by means of FC on silica gel (ethyl acetate/hexane 1:4). The title compound (102.2 g) is obtained in the form of a white solid: m.p. 52–53° C. (recrystallised from diethyl ether/hexane). $R_f$ (ethyl acetate/hexane 1:1)=0.56. Anal. $C_{17}H_{27}BrO_3$ (359.30): calc. C, 56.83; H, 7.57; Br, 22.24; found C, 56.81; H, 7.34; Br, 22.06.

b1) 2(R)-[4-Methoxy-3-(3-methoxypropoxy)-benzyl]-3-methyl-butanol

A solution of 2(R)-[4-methoxy-3-(3-methoxypropoxy)-benzyl]-3-methyl-butyric acid (186 g) in tetrahydrofuran (500 ml) is added slowly at room temperature to a suspension of sodium borohydride (27.2 g) in tetrahydrofuran (1.5 liters). The mixture is stirred until the evolution of gas has ceased (about 45 minutes), and then a solution of iodine (76.2 g) in tetrahydrofuran (1.0 liter) is slowly added and the reaction mixture is stirred at room temperature for a further 4 days. Methanol (1.0 liter) is carefully added dropwise over a period of 20 minutes and after a further 30 minutes' stirring the mixture is concentrated in vacuo. The residue is extracted with ethyl acetate (3×2 liters) and the combined organic phases are washed in succession with 2 liters each of 2N hydrochloric acid, water, saturated sodium thiosulfate solution, water, 0.1N sodium hydroxide solution (1 liter) and saturated sodium chloride solution, dried over magnesium sulfate and concentrated. The residue is purified by FC on silica gel (ethyl acetate/hexane 1:1) and the title compound is obtained in the form of an oil (160 g): $R_f$ (ethyl acetate/hexane 1:1)=0.28. Anal. $C_{17}H_{28}O_4$ (296.41): C, 68.89; H, 9.52; found C, 68.34; H, 9.70.

c1) 2(R)-[4-Methoxy-3-(3-methoxypropoxy)-benzyl]-3-methyl-butyric acid

With ice-cooling, a 30% hydrogen peroxide solution (434 ml) and lithium hydroxide 98% (31.2 g) are added to a solution of 4(R)-benzyl-3-{2(R)-[4-methoxy-3-(3-methoxypropoxy)-benzyl]-3-methyl-butyryl}-oxazolidin-2-one (300 g) in tetrahydrofuran/water 3:1 (4.8 liters). When the addition is complete, the temperature of the reaction mixture is allowed to rise to room temperature over the course of 3 hours; the batch is then cooled again to 0° C. and a 1.5M aqueous sodium sulfite solution (2.55 liters) and then a saturated aqueous sodium hydrogen carbonate solution (1 liter) are added dropwise over the course of 30 minutes. The mixture is concentrated under reduced pressure and the aqueous solution so obtained is washed with dichloromethane (3×3 liters). The aqueous phase is adjusted to pH 3 by the addition of 2N hydrochloric acid, extracted with dichloromethane (3×3 liters), and the combined organic phases are dried over magnesium sulfate and concentrated. The title compound is obtained in the form of an oil (186.8 g), which can be caused to crystallise in hexane/diethyl ether at −20° C.: m.p. 43.5°–44° C. $R_f$ (ethyl acetate/hexane 2:1)=0.30. Anal. $C_{17}H_{26}O_5$ (310.39): calc. C, 65.78; H, 8.44; found C, 65.96; H, 8.70.

d1) 4(R)-Benzyl-3-{2(R)-[4-methoxy-3-(3-methoxypropoxy)-benzyl]-3-methyl-butyryl}-oxazolidin-2-one Under an inert atmosphere at −70° C. a solution of 4(R)-benzyl-3-isovaleroyl-oxazolidin-2-one (156.6 g) in tetrahydrofuran (500 ml) is added to a 1M lithium hexamethyldisilazide solution in tetrahydrofuran (600 ml, 0.60 mol) which has been diluted with anhydrous tetrahydrofuran (600 ml), and the batch is stirred for a further 75 minutes at −70° C. A solution of 4-methoxy-3-(3-methoxypropoxy)-benzyl bromide (145 g) in tetrahydrofuran (500 ml) is then added. The reaction temperature is allowed to rise from −70° C. to 0° C. over a period of 2 hours and the mixture is stirred at 0° C. for a further 18 hours. The reaction is quenched by the addition of a 10% aqueous ammonium chloride solution (250 ml) and the mixture is concentrated under reduced pressure and the aqueous phase is extracted with ethyl acetate (3×1.2 liters). The organic phases are washed with saturated sodium chloride solution, dried over magnesium sulfate and concentrated. Purification of the residue by FC on silica gel (hexane/ethyl acetate 1:1) yields the title compound in the form of a white solid (202 g): m.p. 55°–56° C. (recrystallised from diethyl ether/hexane). $R_f$ (ethyl acetate/hexane 1:2)=0.30. Anal. $C_{27}H_{35}NO_6$ (469.58): calc. C, 69.06; H, 7.51; N, 2.98; found C, 68.64; H, 7.49; N, 3.12.

e1) 4-Methoxy-3-(3-methoxypropoxy)-benzyl bromide

Trimethylsilyl bromide (97 ml) is added dropwise to a solution of 4-methoxy-3-(3-methoxypropoxy)-benzyl alcohol (111.1 g) in chloroform (1.31 liters), the reaction temperature being maintained at 10°–25° C. by cooling with ice. When the addition is complete, the mixture is stirred for a further 10 minutes at room temperature and concentrated under reduced pressure. The residue is purified by FC on silica gel (ethyl acetate/hexane 1:3) and after recrystallisation from hexane the title compound (144.5 g) is obtained in the form of a white crystalline solid: m.p. 50–51° C. $R_f$ (ethyl acetate/hexane 1:2)=0.34.

f1) 4-Methoxy-3-(3-methoxypropoxy)-benzyl alcohol

Sodium borohydride (39.7 g) is added in portions to a solution of 4-methoxy-3-(3-methoxypropoxy)-benzaldehyde (336 g) in methanol (3.36 liters), the reaction temperature being maintained at 0°–5° C. When the addition is complete, the batch is stirred for a further 60 minutes at room temperature and concentrated under reduced pressure, and the residue is partitioned between ice-cooled 2N hydrochloric acid and ethyl acetate (3×2 liters). The combined organic phases are washed with water and saturated sodium hydrogen carbonate solution, added over magnesium sulfate and concentrated. Purification of the residue by FC on silica gel (dichloromethane/methanol 96:4) yields the title compound in the form of an oil (326 g): $R_f$ (ethyl acetate/hexane 2:1)=0.31. Anal. $C_{12}H_{18}O_4$ (226.27): calc. C, 63.70; H, 8.02; found C, 63.70; H, 8.24.

g1) 4-Methoxy-3-(3-methoxypropoxy)-benzaldehyde

A 30% solution of sodium methanolate in methanol (0.86 liter, 4.64 mol) is added dropwise at 61°–64° C. to a solution of 4-methoxy-3-(3-bromopropoxy)-benzaldehyde (844 g) in methanol (4.15 liters). The batch is stirred under reflux for a further 1.5 hours, then allowed to cool to room temperature, and water (150 ml) is added. The methanol is removed in a rotary evaporator (30° C. bath temperature)

and the residue is then partitioned between diethyl ether (3×3 liters) and ice-cold 4N hydrochloric acid. The combined organic phases are washed with water and saturated sodium hydrogen carbonate solution, dried over magnesium sulfate and concentrated. The residue is purified by FC on silica gel (ethyl acetate/hexane 1:3) and the title compound is obtained in the form of an oil (498 g): $R_f$ (ethyl acetate/hexane 1:2)=0.18.

h1) 4-Methoxy-3-(3-bromopropoxy)-benzaldehyde

Potassium carbonate (272.3 g) and 1,3-dibromopropane (1.34 liters) are added to a solution of 3-hydroxy-4-methoxy-benzaldehyde (200 g) in acetonitrile and the white suspension is stirred under reflux for 19 hours. After cooling, the mixture is filtered, the solvent and excess 1,3-dibromopropane are removed under reduced pressure and the residue is purified by FC on silica gel (ethyl acetate/hexane 1:3). The title compound is obtained in the form of a white solid (334 g): $R_f$ (ethyl acetate/hexane 1:1)=0.50. Anal. $C_{11}H_{13}BrO_3$ (273.13): calc. C, 48.37; H, 4.80; Br, 29.26; found C, 48.61; H, 4.84; Br, 29.19.

PREPARATION EXAMPLE 2

2(S)-(tert-butoxycarbonyl)amino-4(S)-[4-methoxy-3-(3-methoxypropoxy)-benzyl]-5-methyl-hexanoic acid ethyl ester With stirring at 0° C., ethyldiisopropylamine (200 ml, 1.1 7 mol) and a solution of di-tert-butyl dicarbonate (216 g, 0.99 mol) in dichloromethane (0.3 liter) are added to a solution of the crude product from Example 1) (351 g) in dichloromethane (2.7 liters). The mixture is stirred for 18 hours at room temperature, then concentrated and the residue is chromatographed on silica gel (eluant gradient ethyl acetate/hexane from 1:4 to 1:2). The crude product so obtained (428 g; approx. 95:5 ratio of title compound to the epimeric 2(R)-(tert-butoxycarbonyl)amino-4(S)-[4-methoxy-3-(3-methoxypropoxy)-benzyl]-5-methyl-hexanoic acid ethyl ester) is recrystallised from hexane. The title compound is obtained in the form of a white crystalline solid (353 g, 81% yield over 3 steps): $R_f$ (1:1 ethyl acetate/hexane)=0.47. M.p. 59°–60° C. IR ($CH_2Cl_2$) 3435, 2960, 1710, 1590, 1515 $cm^{-1}$. $[\alpha]^{25}D=+8.1\pm1.0$(c1, $CH_2Cl_2$). $^1$H-NMR (DMSO-$d_6$ at 80° C.) δ 0.75–0.9 (m, 6H), 1.18 (t, J=7 Hz, 3H), 1.39 (s, 9H), 1.5–1.7 (m, 4H), 1.93 (m, 2H), 2.45 (d, J=6 Hz, 2H), 3.27 (s, 3H), 3.49 (t, J=6.4 Hz, 2H), 3.74 (s, 3H), 4.00 (t, J=6.4 Hz, 2H), 4.0–4.1 (m, 3H), 6.66 (bs, 1H), 6.68 (dd, J=2.8 Hz, 1H), 6.75 (d, J=2 Hz, 1H), 6.84 (d, J=8 Hz, 1H) ppm. Anal. $C_{26}H_{43}NO_7$ (481.63):calc. C, 64.84; H, 9.00; N, 2.91; found C, 65.00; H, 9.16; N, 3.04. The diastereoisomeric purity (>99% de) was determined by high pressure liquid chromatography (HPLC) on a Nucleosil® 5 C18 reversed phase column with an eluant gradient of 20–100% B in 35 minutes (A=water/0.1% trifluoroacetic acid; B=acetonitrile/0.1% trifluoroacetic acid).

PREPARATION EXAMPLE 3

In a manner analogous to that described in Preparation Example 2) it is also possible to prepare the following compounds:

2(S)-(tert-butoxycarbonyl)amino-4(S)-(p-tert-butylphenyl)-5-methyl-hexanoic acid ethyl ester;

2(S)-(tert-butoxycarbonyl)amino-4(R)-(p-tert-butylbenzyl)-hexanoic acid ethyl ester;

2(S)-(tert-butoxycarbonyl)amino-4(S)-[4- tert-butyl-3-(3-methoxypropoxy)-benzyl]-5-methyl-hexanoic acid ethyl ester;

2(S)-(tert-butoxycarbonyl)amino-4(S)-[3-benzyloxy-4,5-ethylenedioxy-benzyl]-5-methyl-hexanoic acid ethyl ester;

2(S)-(tert-butoxycarbonyl)amino-4(S)-[4-ethyl-3-(3-methoxypropoxy)-benzyl]-5-methyl-hexanoic acid ethyl ester;

2(S)-(tert-butoxycarbonyl)amino-4(S)-[3-benzyloxy-4-methoxy-benzyl]-5-methyl-hexanoic acid ethyl ester;

2(S)-(tert-butoxycarbonyl)amino-4(S)-[4-benzyloxy-3-(3-methoxy-propoxy)-benzyl]-5-methyl-hexanoic acid ethyl ester.

The starting materials can be prepared, for example, in a manner analogous to that described in Preparation Examples 1) and 1b) starting from the intermediates described in Preparation Example 5).

PREPARATION EXAMPLE 4

2(S)-(tert-butoxycarbonyl)amino-4(S)-benzyloxymethyl-5-methyl-hexanoic acid ethyl ester A mixture of 2(S)-[2(S)-benzyloxymethyl-3-methylbutyl]-3,6-diethoxy-2,5-dihydro-pyrazine (1.20 g, 3.33 mmol), acetonitrile (12 ml) and 1N hydrochloric acid (12 ml) is stirred at room temperature for 20 minutes and then poured into a saturated sodium hydrogen carbonate solution (50 ml). The mixture is extracted with dichloromethane (3×60 ml), and the combined organic phases are washed with water (3×100 ml) and concentrated to a volume of 15 ml. The solution so obtained is cooled to 0° C., and ethyldiisopropylamine (0.73 ml, 4.29 mmol) and a solution of di-tert-butyl dicarbonate (0.79 g, 3.63 mmol) in dichloromethane (2 ml) are added. The batch is stirred at room temperature for 16 hours and after concentration of the solvent the residue is purified by flash chromatography (100 g of silica gel, 1:6 ethyl acetate/hexane). The title compound is obtained in admixture with the epimeric 2(R)-(tert-butoxycarbonyl)amino-4(S)-benzyloxymethyl-5-methyl-hexanoic acid ethyl ester (1.23 g, 94%; approx. 2:1 diastereoisomer ratio) in the form of a colourless oil: $R_f$ (ethyl acetate/hexane 1:4)=0.34. $^1$H-NMR (CDCl$_3$): δ 0.85–0.9 (m, 6H), 1.25–1.3 (m, 3H), 1.42 (s, 9H), 1.55–1.9 (m, 4H), 3.25–3.5 (m, 2H), 4.1–4.35 (m, 3H), 4.45–4.55 (m, 2H), 5.35 (d, 0.33H), 5.43 (d, 0.67H), 7.25–7.4 (m, 5H) ppm. Anal. $C_{22}H_{35}NO5$ (393.52): calc. C, 67.15; H, 8.96; N, 3.56; found C, 66.88; H, 8.67; N, 3.50.

The starting material can be prepared, for example, as follows:

a) 2(S)-[2(S)-Benzyloxymethyl-3-methylbutyl]-3,6-diethoxy-2,5-dihydro-pyrazine 1.6M n-butyllithium in hexane (3.5 ml, 5.6 mmol) is added dropwise under an inert atmosphere at −40° C. to a solution of 3,6-diethoxy-2,5-dihydro-pyrazine (1.02 g, 6.0 mmol) in tetrahydrofuran. After 15 minutes' stirring, a solution of 2(S)-benzyloxymethyl-3-methylbenzyl bromide (1.09 g, 4.0 mmol) in tetrahydrofuran (5 ml) is added dropwise at −40° C. and the reaction mixture is then left to stand at −18° C. for 16 hours. The batch is concentrated and the residue is partitioned between ethyl acetate (30 ml) and water (30 ml). The aqueous phase is extracted with ethyl acetate (2×30 ml) and the combined organic phases are washed with saturated sodium chloride solution, dried over magnesium sulfate and concentrated. The crude product is purified by flash chromatography (100 g of silica gel, 1:6 ethyl acetate/hexane). The title compound (1.28 g, 89%) is obtained in admixture with the 2(R)-[2(S)- benzyloxymethyl-3-methylbutyl]-3,6-diethoxy-2,5-dihydro-pyrazine diastereoisomer (approx. 2:1 diastereoisomer ratio on the basis of the $^1$H-NMR spectrum) in the form of a pale-yellow oil: $R_f$ (ethyl acetate/hexane 1:4)=0.32. $^1$H-NMR (CDCl$_3$): δ 5 0.75–0.9 (m, 6H), 1.2–1.35 (m, 6H), 1.4–2.05 (m, 4H), 3.35–3.55 (m, 2H), 3.95–4.15 (m, 7H), 4.47 (s, 0.34H), 4.50 (s, 0.66H), 7.25–7.4 (m, 5H) ppm.

PREPARATION EXAMPLE 5

1-Bromo-2(R)-isopropyl-3-(p-tert-butyl-phenyl)-propane

Triphenylphosphine (3.15 g) and then, in portions, N-bromosuccinimide (2.14 g) are added at 0° C., with stirring, to a solution of 2(R)-(p-tert-butyl-benzyl)-3-methyl-butanol (2.3 g) in dichloromethane (50 ml). The reaction mixture is then stirred for 16 hours at room temperature and concentrated. The title compound is obtained from the residue by FC purification (100 g of silica gel, eluant dichloromethane/hexane 1:1): $R_f$ (hexane)=0.49.

The starting materials can be prepared, for example, as follows:

a) 2(R)-(p-tert-butyl-benzyl)-3-methyl-butanol

A solution of 4(R)-benzyl-3-[2(R)-(p-tert-butyl-benzyl)-3-methyl-butyryl]-oxazolidin-2-one (8.63 g) in tetrahydrofuran (40 ml) is added dropwise at 0° C., with stirring, to a suspension of lithium aluminium hydride (2.41 g) in tetrahydrofuran (160 ml). The reaction mixture is stirred for 4 hours at 0° C. and then, at 0° C., ethyl acetate (5 ml), 30 ml of a (1:1) mixture of tetrahydrofuran/water and 2N sulfudc acid (80 ml) are added in succession thereto. The supension is extracted with ethyl acetate and the crude product is purified by FC (700 g of silica gel, eluant dichloromethane). The title compound is obtained: $R_f$ (dichloromethane)=0.34; m.p. 49°–51° C.

b) 4(R)-Benzyl-3-[2(R)-(p-tert-butyl-benzyl)-3-methyl-butyryl]-oxazolidin-2-one

A solution of 4(R)-benzyl-3-isovaleroyl-oxazolidin-2-one (13.2 g) in tetrahydrofuran (20 ml) is added dropwise under an inert atmosphere, with stirring, at −70° C. to a 1M lithium hexamethyldisilazide solution in tetrahydrofuran (31 ml) which has been diluted with tetrahydrofuran (30 ml), and the reaction mixture is stirred at −70° C. for 1 hour. A solution of p-tert-butyl-benzyl bromide (9.6 g) in tetrahydrofuran (20 ml) is then added dropwise and the mixture is stirred for a further one hour at −25° C. and for 4 hours at 0° C. 6 ml of a saturated ammonium chloride solution are added to the reaction mixture which is then freed of tetrahydrofuran by concentration under reduced pressure and extracted with diethyl ether. The title compound is obtained from the residue of the extract by purification by means of FC (700 g of silica gel, eluant dichloromethane/hexane 1:1): $R_f$ (dichloromethane/hexane 1:1)=0.30; m.p. 123.5°–124° C.

In an analogous manner it is also possible to prepare the following compounds of formula XV:

1-bromo-2(S)-ethyl-3-(p-tert-butylphenyl)-propane;
1-bromo-2(R)-isopropyl-3-(p-tert-butylphenyl)-propane;
1-bromo-2(R)-isopropyl-3-[3-benzyloxy-4,5-ethylenedioxy-phenyl]-propane;
1-bromo-2(R)-isopropyl-3-[4-benzyloxy-3-(3-methoxy-propoxy)-phenyl]-propane;
1-bromo-2(R)-isopropyl-3-[4-tert-butyl-3-(3-methoxy-propoxy)-phenyl]-propane;
1-bromo-2(R)-isopropyl-3-[4-ethyl-3-(3-methoxy-propoxy)-phenyl]-propane;
1-bromo-2(R)-isopropyl-3-[4-methoxy-3-benzyloxy-phenyl]-propane.

PREPARATION EXAMPLE 6

2(S)-(Tert-Butoxycarbonyl)Amino-4(S)-[4-methoxy-3-(3-methoxy-propoxy)-benzyl]-5-methyl-hexan-1-ol Lithium borohydride (3.0 g, 138 mmol) is added in one portion at room temperature to a solution of the product from Preparation Example 2) (28.9 g, 60 mmol) in tetrahydrofuran (430 ml) and the batch is stirred for a further 16 hours. Methanol is then added dropwise and the mixture is concentrated in a rotary evaporator (40° C. bath temperature), and 400 ml of a mixture of 1N hydrochloric acid and ice are added to the residue. The mixture is extracted with dichloromethane (3×400 ml), and the combined organic phases are dried over magnesium sulfate and concentrated. Recrystallisation of the crude product from diethyl ether/hexane yields the title compound in the form of a white crystalline solid (25.2 g, 95%): m.p. 66°–67° C. $R_f$ (ethyl acetate/hexane 1:1)=0.19. IR (CH$_2$Cl$_2$) 3435, 2960, 1710, 1590, 1515, 1465 cm$^{-1}$. [α]$^{25}$D=+1.8±1.0 (c1, CH$_2$Cl$_2$). $^1$H-NMR (DMSO-d$_6$ at 80° C.): δ 0.65–0.8 (m, 6H), 1.25–1.4 (m, 2H), 1.41 (s, 9H), 1.6–1.65 (m, 2H), 1.93 (m, 2H), 2.33 (dd, J=9, 14 Hz, 1H), 2.60 (dd, J=6, 14 Hz, 1H), 3.26 (s, 3H), 3.25–3.35 (m, 2H), 3.49 (t, J=6.4 Hz, 2H), 3.35–3.55 (m, 1H), 3.74 (s, 3H), 4.01 (t, J=6.4 Hz, 2H), 4.19 (t, J=6 Hz), 5.98 (br d, 1H), 6.70 (dd, J=2, 8 Hz, 1H), 6.80 (d, J=2 Hz, 1H), 6.82 (d, J=8 Hz, 1H) ppm. Anal. C$_{24}$H$_{41}$NO$_6$ (439.59): calc. C, 65.58; H, 9.40; N, 3.19; found C, 65.52; H, 9.19; N, 3.21.

PREPARATION EXAMPLE 7

2(S)-(-tert-butoxycarbonyl)amino-4(S)-[4-methoxy-3-(3-methoxy-propoxy)-benzyl]-5-methyl-hexanal At 0° C., first triethylamine (175.6 ml) and then a solution of pyridine/sulfur trioxide complex (221 g) in dimethyl sulfate (0.84 liters) are added dropwise over a period of 45 minutes, with stirring, to a solution of 2(S)-(tert-butoxycarbonyl)amino-4(S)-[4-methoxy-3-(3-methoxypropoxy)-benzyl]-5-methyl-hexanol (184.8 g) in dichloromethane (1.34 liters). When the addition is complete, the batch is stirred for a further 30 minutes at 0° C. and then ice-water (1.6 liters) is added. The mixture is extracted with dichloromethane (3×1.6 liters), and the combined organic phases are washed with saturated sodium hydrogen carbonate solution (2×1.6 liters), water (1.6 liters) and saturated sodium chloride solution and filtered through cotton wool and the solvent is removed in vacuo. The residue is dried under a high vacuum, yielding the crude title compound in the form of an oil (190 g): $R_f$ (ethyl acetate/hexane 1:1)=0.44. IR (CH$_2$Cl$_2$) 3430, 2960, 1710, 1589, 1515 cm$^-$. $^1$H-NMR (CDCl$_3$): δ 0.86 (m, 6H), 1.44 (s, 9H), 1.55–1.8 (m, 4H), 2.09 (m, 2H), 2.4–2.7 (m, 2H), 3.35 (s, 3H), 3.57 (t, J=6.4 Hz, 2H), 3.83 (s, 3H), 4.10 (t, J=6.4 Hz, 2H), 4.05–4.20 (m, 1H), 4.89 (d, br., 1), 6.7–6.8 (m, 3H), 9.50 (s, 1H).

PREPARATION EXAMPLE 8

2(S)-(tert-butoxycarbonyl)amino-4(S)-(p-tert-butyl-benzyl)-5-methyl-hexanal

A 1.2M diisobutylal hydridesolution in toluene (4.2 ml) is slowly added dropwise at −75° C. to a solution of 2(S)-(tert-butoxycarbonyl)amino-4(S)-(p-tert-butyl-benzyl)-5-methyl-hexanoic acid ethyl ester (1 g) in toluene (20 ml). The reaction mixture is stirred for 30 minutes at −70° C., then 10 ml of methanol are added and the mixture is poured onto a mixture of ice and 1N hydrochloric acid (10 ml) and extracted with ethyl acetate. The title compound is obtained: $R_f$ (dichloromethane)=0.35.

The following compounds can be prepared in the same manner:

2(S)-(tert-butoxycarbonyl)amino-4(R)-(p-tert-butyl-benzyl)-hexanal;

2(S)-(tert-butoxycarbonyl)amino-4(S)-[4-tert-butyl-3-(3-methoxypropoxy)-benzyl]-5-methyl-hexanal;

2(S)-(tert-butoxycarbonyl)amino-4(S)-[3-benzyloxy-4-5-ethylenedioxy-benzyl]-5-methyl-hexanal;

2(S)-(tert-butoxycarbonyl)amino-4(S)-[4-ethyl-3-(3-methoxypropoxy)-benzyl]-5-methyl-hexanal;

2(S)-(tert-butoxycarbonyl)amino-4(S)-[4-methoxy-3-benzyloxy-benzyl]-5-methyl-hexanal;

2(S)-(tert-butoxycarbonyl)amino-4(S)-[4-benzyloxy-3-(3-methoxy-propoxy)-benzyl]-5-methyl-hexanal;

APPLICATION EXAMPLE 1

5(S)-Amino-4(S)-hydroxy-2(S)-isopropyl-7(S)-[4-methoxy-3-(3-methoxy-propoxy)-benzyl]-8-methyl-nonanoic acid (2-morpholin-4-yl-ethyl)amide dihydrochloride 3.09 g of 5(S)-(tert-butoxycarbonyl)amino-4(S)-hydroxy-2(S)-isopropyl-7(S)-[4-methoxy-3-(3-methoxy-propoxy)-benzyl]-8-methyl-nonanoic acid N-(2-morpholin-4-yl-ethyl) amide are dissolved in 4N hydrochloric acid in dioxane (40 ml) at 0° C. and stirred at that temperature for 2 hours. The reaction mixture is lyophilized and the title compound is obtained: $R_f$ (dichloromethane/methanol 8:2)=0.27; HPLC $R_f$=9.52 min; FAB-MS (M+H)$^+$=566.

The starting materials are prepared as follows:

a) 5(S)-tert-butoxycarbonyl)amino-4(S)-hydroxy-2(S)-isopropyl7(S)-[4-methoxy-3-(3-methoxy-propoxy)-benzyl]-8-methyl-nonanoic acid N-(2-morpholin-4-yl-ethyl)amide A mixture of N-(tert-butoxycarbonyl)amino-2(S)-{4(S)-[2(S)-[4-methoxy-3-(3-methoxy-propoxy)-benzyl]-3-methyl-butyl]-2,2-dimethyl-oxazolidin-5(S)-ylmethyl}-3-methyl-N-(2-morpholin-4-yl-ethyl)-butyramide (4.18 g) and p-toluenesulfonic acid monohydrate (1.30 g) in methanol (160 ml) is stirred for 1 hour at 0° C. and for a further 18 hours at room temperature. After removal of the solvent, 0.1N sodium hydroxide (200 ml) is added to the residue and the mixture is extracted with dichloromethane. After concentration of the organic phases, the crude product is purified by FC (230 g of silica gel, dichloromethane/-methanol 95:5). The title compound is obtained: $R_f$ (dichloromethane/methanol 9:1)=0.55.

b) N-(tert-butoxycarbonyl)amino2(S)-{4(S)-[2(S)-[4-methoxy-3-(3-methoxypropoxy)-benzyl]-3-methyl-butyl]-2,2-dimethyl-oxazolidin-5(S)-yl-methyl}-3-methyl-N-(2-morpholin-4-yl-ethyl)-butyramide Triethylamine (1.09 ml), 4-(2-aminoethyl)-morpholine (1.02 ml) and cyanophosphonic acid diethyl ester (1.19 ml) are added in succession at 0° C., with stirring, to a solution of N-(tert-butoxycarbonyl)amino-2(S)-{4(S)-[2(S)-[4-methoxy-3-(3-methoxypropoxy)-benzyl]-3-methyl-butyl]-2,2-dimethyl-oxazolidin-5(S)-ylmethyl}-3-methyl-butyric acid (3.88 g) in N,N-dimethylformamide (190 ml). The batch is stirred for 18 hours at room temperature, then concentrated under reduced pressure and the residue is partitioned between diethyl ether and saturated sodium hydrogen carbonate solution. The organic phases are washed with saturated sodium chloride solution and concentrated by evaporation. The evaporation residue is purified by FC (230 g of silica gel, dichloromethane/methanol 95:5) and the title compound is obtained: $R_f$ (dichloromethane/methanol 95:5) =0.25.

c) N-(tert-butoxycarbonyl)amino2(S)-{4(S)-[2(S)-[4-methoxy-3-(3-methoxypropoxy)-benzyl]-3-methyl-butyl]-2,2-dimethyl-oxazolidin-5(S)-ylmethyl}-3-methyl-butyric acid Water (470 ml), potassium permanganate (79.1 g) and tetrabutylammonium bromide (9.7 g) are added in succession at 0° C., with stirring, to a solution of N-(tert-butoxycarbonyl)amino-2(S)-{4(S)-[2(S)-[4-methoxy-3-(3-methoxypropoxy)-benzyl]-3-methyl-butyl]-2,2-dimethyloxazolidin-5(S)-ylmethyl}-3-methyl-butyraldehyde (53.0 g) in toluene (470 ml). The reaction mixture is stirred for 48 hours at 0°–5° C. and then, at 10% sodium sulfite solution (1.2 liters) and, after a further 30 minutes, 10% citric acid solution (1.95 liters) and water (1.2 liters) are added. The mixture is extracted with ethyl acetate (3×2.5 liters), and the organic phases are washed with water and saturated sodium chloride solution, dried over magnesium sulfate and concentrated. Purification of the crude product by FC (2.3 kg of silica gel, ethyl acetate/hexane 3:7) yields the pure title compound in the form of an oil (31.7 g): $R_f$ (ethyl acetate/hexane 1:2)=0.21; Anal. $C_{33}H_{55}NO_8$ (593.80): calc. C, 66.75; H, 9.34; N, 2.36; found C, 66.69; H, 9.39; N, 2.39.

d) N-(tert-butoxycarbonyl)amino2(S)-{4(S)-[2(S)-[4-methoxy-3-(3-methoxypropoxy)-benzyl]-3-methyl-butyl]-2,2-dimethyl-oxazolidin-5(S)-yl-methyl}-3-methyl-butyraldehyde Tetrapropylammonium perruthenate (1.60 g) is added at room temperature to a mixture of N-(tert-butoxycarbonyl) amino-2(S)-{4(S)-[2(S)-[4-methoxy-3-(3-methoxypropoxy) -benzyl]-3-methyl-butyl]-2,2-dimethyl-oxazolidin-5(S)-ylmethyl}-3-methyl-butan-1-ol (53.0 g), N-methylmorpholine N-oxide (16.6 g) and 100 g of molecular sieve (0.3 nm) in dichloromethane (1.8 liters) and the batch is stirred for 30 minutes. The mixture is filtered, diluted with dichloromethane and the filtrate is washed in succession with 2M sodium sulfite solution, saturated sodium chloride solution and 1M copper(II) sulfate solution. After drying over magnesium sulfate, the organic phase is concentrated and the title compound is obtained in the form of a crude product: $R_f$ (ethyl acetate/hexane 1:2)=0.43.

e) N-(tert-butoxycarbonyl)amino2(S)-{4(S)-[2(S)-[4-methoxy-3-(3-methoxypropoxy)-benzyl]-3-methyl-butyl]-2,2-dimethyl-oxazolidin-5(S)-yl-methyl}-3-methyl-butane-1-ol A solution of N-(tert-butoxycarbonyl)amino-4(S)-{2(S)-[4-methoxy-3-(3-methoxypropoxy)-benzyl]-3-methyl-butyl}-5(S)-[2(S)-benzyloxymethyl-3-methyl-butyl]-2,2-dimethyl-oxazolidine (3.7 g) in tertahydrofuran (50 ml) is hydrogenated in presence of 5% Pd/C (1.0 g) for 15 minutes at room temperature and under normal pressure. The reaction mixture is filtered and the filtrate is concentrated. The residue is purified by FC (140 g of silica gel, ethyl acetate/ hexane 1:2) and the title compound is obtained in the form of a colourless oil (2.92 g): $R_f$ (ethyl acetate/hexane 1:2)= 0.28; Anal. $C_{33}H_{57}NO_7$ (579.82): calc. C, 68.36; H, 9.91; N, 2.42; found C, 67.78; H, 9.82; N, 2.30.

f) N-(tert-butoxycarbonyl)amino4(S){2(S)-[4-methoxy-3-(3-methoxypropoxy)-benzyl-3-methyl-butyl}-5(S)-2(S)-benzyloxymethyl-3-methyl-butyl]2,2-dimethyl-oxazolidine (diastereoisomer A) and N-(tert-butoxycarbonyl)amino-4(S) -{2(S)-[4-methoxy-3-(3-methoxypropoxy)-benzyl]-3- methyl-butyl}-5(R)-[2(S)-benzyloxymethyl-3-methyl-butyl]-2,2-dimethyloxazolidine (diastereoisomer B)

2,2-Dimethoxypropane (10.9 ml) and p-toluenesulfonic acid monohydrate (10 mg) are added at room temperature to a solution of 3(S)-benzyloxymethyl-6(S)-(tert-butoxycarbonyl)amino-8(S)-[4-methoxy-3-(3-methoxypropoxy)-benzyl]-2,9dimethyl-decan-5(R,S)-ol (7.0 g) in dichloromethane (1.86 liters). After being stirred for 24 hours at room temperature, the batch is concentrated and the residue is purified by FC (1 kg of silica gel, dichloromethane/diethyl ether 96:4). The two title compounds are obtained, each in the form of a colourless oil. Diastereoisomer A (3.72 g): $R_f$ (dichloromethane/tert-butyl methyl ether 95:5)=0.36. Diastereoisomer B (2.68 g): $R_f$ (dichloromethane/tert-butyl methyl ether 95:5)=0.44.

g) 3-(S)-Benzyloxymethyl-6(S)-(tert-butoxycarbonyl) amino-8(S)-[4-methoxy-3-(3-methoxypropoxy)-benzyl]-2,9-dimethyl-decan-5(R,S)-ol 51.1 g of magnesium chips are placed in tetrahydrofuran (1.4 liters) at 55° C. Then over a period of 30 minutes a solution of 2(S)-bromomethyl-3-methyl-butyl-benzyl ether (380 g) and 1,2-dibromoethane (30.2 ml) in tetrahydrofuran (0.8 liter) is added dropwise at 55° C.

The reaction mixture is stirred for a further 20 minutes at 55° C. and then cooled to 5° C. A solution of 2(S)-(tert-butoxycarbonyl)amino-4(S)-[4-methoxy-3-(3-methoxypropoxy)-benzyl]-5-methyl-hexanal (190 g) in tetrahydrofuran (700 ml) is then added dropwise. The reaction mixture is stirred for a further 3 hours at room temperature, then at 5° C. saturated ammonium chloride solution is added and the mixture is extracted with diethyl ether. The organic phases are concentrated and purified by FC (4 kg of silica gel, ethyl acetate/hexane 1:3). The title compound is obtained in the form of a colourless oil (139 g): $R_f$ (ethyl acetate/hexane 1:2)=0.26; HPLC $R_t$=22.7 and 22.8 min ((4:6)-diastereoisomeric mixture).

APPLICATION EXAMPLE 2

5(S)-Amino-7(S)-(p-tert-butyl-benzyl)-4(S)-hydroxy-2(R,S), 8-dimethyl-nonanoic acid N-(butyl)amide hydrochloride 111 mg of 5(S)-(tert-butoxycarbonyl)amino-7(S)-(p-tert-butyl-benzyl)-4(S)-hydroxy-2(R,S),8-dimethyl-nonanoic acid N-(butyl)amide are dissolved in 4N hydrochloric acid in dioxane (2 ml) at 0° C. and stirred for 60 minutes at 20° C. The reaction mixture is concentrated by evaporation under reduced pressure and the residue is purified by FC (50 g of silica gel, dichloromethane/methanol 9:1). The title compound is obtained in the form of a diastereoisomeric mixture: $R_f$ (dichloromethane/methanol 9:1)=0.20; $R_t$(I)= 36.6 and 37.5 min; FAB-MS (M+H)$^+$=419.

The starting materials can be prepared, for example, as follows:

a) 5(S)-(tert-butoxycarbonyl)amino7(S)-(p-tert-butyl-benzyl)-4(S)-hydroxy-2(R,S),8-dimethyl-nonanoic acid N-(butyl)amide 150 mg of 2-[3(S)-(tert-butoxycarbonyl)amino-5(S)-(p-tert-butyl-benzyl)-2(S)-hydroxy-6-methyl-heptyl]-N-butyl-acrylamide (diastereoisomer I, Application Example 2b) are hydrogenated in the presence of 150 mg of 10% Pd/C in tetrahydrofuran (20 ml) for 2 hours at room temperature and under normal pressure. The reaction mixture is filtered and concentrated by evaporation. The residue is purified by FC (50 g of silica gel, dichloro-methane/diethyl ether 8:2). The title compound is obtained in the form of a diastereoisomeric mixture: $R_f$ (dichloromethane/diethyl ether 8:2)=0.18.

b) 2-[3(S)-(tert-butoxycarbonyl)amino5(S)-(p-tert-butyl-benzyl)-2(S)-hydroxy-6-methyl-heptyl]-N-butyl-acrylamide 695 mg of methacrylic acid butylamide are dissolved in tetrahydrofuran (30 ml) and at −75° C. a 1.6M n-butyllithium solution in hexane (6.2 ml) is added. The reaction mixture is stirred for 30 minutes at 0° C. and then at −75° a 1M chlorotitanium triisopropanolate solution in hexane (9.8 liters) is added. The batch is stirred for a further 15 minutes at −75° C. and then at the same temperature a solution of 2(S)-(tert-butoxycarbonyl)amino-4(S)-(p-tert-butyl-benzyl)-5-methyl-hexanal (924 mg) in tetrahydrofuran (10 ml) is added dropwise. The reaction mixture is stirred for a further 15 minutes at −75° C. and for 70 minutes at 0° C. and then 10% aqueous citric acid solution (15 ml), water and diethyl ether are added in succession thereto. The mixture is extracted repeatedly with diethyl ether and the crude diastereoisomeric mixture is then separated by FC (700 g of silica gel, dichloromethane/diethyl ether 9:1). The title compound (diastereoisomer I): $R_f$ (dichloromethane/diethyl ether 9:1)=0.21; and the C-2 epimeric diastereoisomer II $R_f$ (dichloromethane/diethyl ether 9:1)=0.14 are obtained.

APPLICATION EXAMPLE 3

5(S)-Amino-7(S)-[4-methoxy-3-(3-methoxypropoxy)-benzyl]-4(S)-hydroxy-2(R),8-dimethyl-nonanoic acid N-(butyl)amide hydrochloride In a manner analogous to that described in Application Example 2), the title compound is prepared starting from 27 mg of 5(S)-(tert-butoxycarbonyl)amino-7(S)-[4-methoxy-3-(3-methoxypropoxy)-benzyl]-4(S)-hydroxy-2(R),8-dimethyl-nonanoic acid N-(butyl)amide and purified by FC (2 g of silica gel, dichloromethane/methanol 95:5): $R_f$ (dichloromethane/methanol 9:1)=0.15; $R_t$(I)=21.9 min; high-resolution FAB-MS(M+H)$^+$: calc. 481.3641; found 481.3636.

The starting material is prepared starting from 5(S)-(tert-butoxycarbonyl)amino-4(S)-hydroxy-7(S)-(3-hydroxy-4-methoxy-benzyl)-2(R),8-dimethyl-nonanoic acid N-(butyl) amide by reaction first with sodium hydride in N,N-dimethylformamide (30 minutes at room temperature) followed by alkylation with 3-methoxy-propyl iodide (24 hours' stirring at room temperature) according to customary methods.

The 5(S)-(tert-butoxycarbonyl)amino-4(S)-hydroxy-7(S) -(3-hydroxy-4-methoxy-benzyl)-2(R),8-dimethyl-nonanoic acid N-(butyl)amide used as starting material can be prepared, for example, as follows:

a) 5(S)-tert-butoxycarbonylamino4(S)-hydroxy-7(S)-(3-hydroxy-4-methoxy-benzyl)-2(R), 8-dimethyl-nonanoic acid N-(butyl)amide A solution of 5(S)-(tert-butoxycarbonyl)amino-4(S)-hydroxy-7(S)-(3-benzyloxy-4-methoxy-benzyl)-2(R),8-dimethyl-nonanoic acid N-(butyl)amide (4.7 g) in methanol (60 ml) is hydrogenated in the presence of 10% Pd/C (2.35 g) at room temperature and under normal pressure for 1 hour. Filtration, concentration of the filtrate and drying under a high vacuum yield the title compound: $R_f$ (hexane/ethyl acetate 1 )=0.15; FAB-MS (M+H)$^+$=509.

b) 5(S)-(tert-butoxycarbonyl)amino-4(S)-hydroxy-7(S)-(3-benzyloxy-4-methoxy-benzyl)-2(R),8-dimethyl-nonanoic acid N-(butyl)amide A solution of 2-[3(S)-(tert-butoxycarbonyl)amino-5(S)-(3-benzyloxy-4-methoxy-benzyl)-2(S)-hydroxy-6-methylheptyl]-N-butyl-acrylamide (3.5 g) in absolute methanol (30 ml) is hydrogenated under an inert atmosphere in the presence of 20 mg of [Ru₂Cl₄((S)-BINAP)₂]·NEt₃ at room temperature and 25 bar for 5 hours. The reaction mixture is filtered and after concentration of the filtrate the residue is purified by FC (200 g of silica gel, hexane/ethyl acetate 1:1). The title compound is obtained: $R_f$ (hexane/ethyl acetate 1:1)=0.16; FAB-MS (M+H)⁺=599.

The 2-[3(S)-(tert-butoxycarbonyl)amino-5(S)-(3-benzyloxy-4-methoxy-benzyl)-2(S)-hydroxy-6-methyl-heptyl]-N-butyl-acrylamide used as starting material is prepared in a manner analogous to that described in Application Example 2b) starting from 2(S)-(tert-butoxy-carbonyl)amino-4(S)-[4-methoxy-3-(3-methoxypropoxy)-benzyl]-5-methyl-hexanal.

What is claimed is:

1. A compound of formula Ib

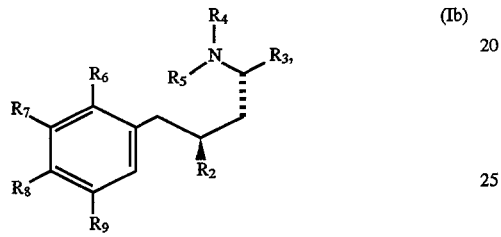

wherein $R_2$ is lower alkyl, 3- to 8-membered cycloalkyl, 3- to 8-membered cycloalkyl-lower alkyl, or a lower alkyl radical that is unsubstituted or substituted in the phenyl, naphthyl or heteroaryl moiety by lower alkyl, lower alkoxy, halogen and/or by trifluoromethyl, $R_3$ is formyl, hydroxymethyl, carboxy, lower alkoxycarbonyl, lower alkenyloxycarbonyl or an unsubstituted or lower alkyl-, lower alkoxy-, halo- and/or trifluoromethyl-substituted phenyl-lower alkoxycarbonyl or phenyloxycarbonyl radical, $R_4$ is hydrogen, lower alkyl, an unsubstituted or lower alkyl-, lower alkoxy, halo- and/or trifluoromethyl-substituted phenyl- or naphthyl-lower alkyl radical, lower alkanoyl, tri-halo-lower alkanoyl, an unsubstituted or lower alkyl-, lower alkoxy-, halo-, trifluoromethyl- and/or nitro-substituted benzoyl or phenyl-lower alkoxycarbonyl group, tri-lower alkylsilyl or benzyl-(di-lower alkyl)silyl, $R_5$ is hydrogen or lower alkyl, $R_6$ is hydrogen, hydroxy, lower alkoxy, cycloalkoxy, lower alkoxy-lower alkoxy, carboxy-lower alkoxy, lower alkoxycarbonyl-lower alkoxy, carbamoyl-lower alkoxy or N-mono- or N,N-di-lower alkylcarbamoyl-lower alkoxy, $R_7$ is hydrogen, lower alkyl, cycloalkyl, lower alkoxy-lower alkyl, lower alkoxy-lower alkoxy-lower alkyl, cycloalkoxy-lower alkyl, hydroxy, lower alkanoyloxy-lower alkyl, hydroxy-lower alkoxy, halo-(hydroxy)-lower alkoxy, lower alkanesulfonyl-(hydroxy)-lower alkoxy, amino-lower alkyl, lower alkylamino-lower alkyl, di-lower alkylamino-lower alkyl, lower alkanoylamino-lower alkyl, lower alkoxycarbonylamino-lower alkyl, lower alkoxyimino-lower alkyl, amino-lower alkoxy, lower alkylamino-lower alkoxy, di-lower alkylamino-lower alkoxy, lower alkanoylamino-lower alkoxy, lower alkoxycarbonylamino-lower alkoxy, oxo-lower alkoxy, lower alkoxy, cycloalkoxy, lower alkenyloxy, cycloalkoxy-lower alkoxy, lower alkoxy-lower alkoxy, lower alkoxy-lower alkenyl, lower alkenyloxy-lower alkoxy, lower alkoxy-lower alkenyloxy, lower alkenyloxy-lower alkyl, lower alkanoyl-lower alkoxy, lower alkylthio-lower alkoxy, lower alkanesulfonyl-lower alkoxy, lower alkylthio-(hydroxy)-lower alkoxy, aryl-lower alkoxy, thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, cyano-lower alkoxy, lower alkoxycarbonyl-lower alkoxy, carbamoyl-lower alkoxy, N-mono- or N,N-di-lower alkylcarbamoyl-lower alkoxy, carboxy-lower alkyl, lower alkoxycarbonyl-lower alkyl, carbamoyl-lower alkyl or N-mono- or N,N-di-lower alkylcarbamoyl-lower alkyl, $R_8$ is lower alkyl, polyhalo-lower alkyl, lower alkoxy-lower alkyl, cycloalkoxy-lower alkyl, hydroxy-lower alkyl, lower alkylthio-lower alkyl, lower alkanesulfonyl-lower alkyl, optionally partially hydrogenated or N-oxidised pyridyl-lower alkyl, thiazolylthio-lower alkyl or thiazolinylthio-lower alkyl, imidazolylthio-lower alkyl, optionally N-oxidised pyridylthio-lower alkyl, pyrimidinylthio-lower alkyl, amino-lower alkyl, lower alkylamino-lower alkyl, di-lower alkylamino-lower alkyl, lower alkanoylamino-lower alkyl, lower alkanesulfonylamino-lower alkyl, polyhalo-lower alkanesulfonylamino-lower alkyl, pyrrolidino-lower alkyl, piperidino-lower alkyl, piperazino-, N'-lower alkylpiperazino- or N'-lower alkanoylpiperazino-lower alkyl, morpholino-lower alkyl, thiomorpholino-, S-oxothiomorpholino- or S,S-dioxothiomorpholino-lower alkyl, cyano-lower alkoxy, carboxy-lower alkyl, lower alkoxycarbonyl-lower alkyl, carbamoyl-lower alkyl, N-mono- or N,N-di-lower alkylcarbamoyl-lower alkyl, cycloalkyl; phenyl or naphthyl that is unsubstituted or mono-, di- or tri-substituted by lower alkyl, lower alkoxy, hydroxy, lower alkylamino, di-lower alkylamino, halogen and/or by trifluoromethyl; hydroxy, lower alkoxy, cycloalkoxy, lower alkoxy-lower alkoxy, cycloalkoxy-lower alkoxy, hydroxy-lower alkoxy; phenyl-lower alkoxy or naphthyl-lower alkoxy that is unsubstituted or mono-, di- or tri-substituted by lower alkyl, lower alkoxy, hydroxy, lower alkylamino, di-lower alkylamino, halogen and/or by trifluoromethyl; lower alkoxy, polyhalo-lower alkoxy, lower alkylthio-lower alkoxy, lower alkanesulfonyl-lower alkoxy, optionally hydrogenated heteroaryl-lower alkoxy, optionally partially or fully hydrogenated heteroarylthio-lower alkoxy, such as thiazolylthio-lower alkoxy or thiazolinylthio-lower alkoxy, imidazolylthio-lower alkoxy, optionally N-oxidised pyridylthio-lower alkoxy, pyrimidinylthio-lower alkoxy, amino-lower alkoxy, lower alkylamino-lower alkoxy, di-lower alkylamino-lower alkoxy, lower alkanoylamino-lower alkoxy, lower alkanesulfonylamino-lower alkoxy, polyhalo-lower alkanesulfonylamino-lower alkoxy, pyrrolidino-lower alkoxy, piperidino-lower alkoxy, piperazino-, N'-lower alkylpiperazino- or N'-lower alkanoylpiperazino-lower alkoxy, morpholino-lower alkoxy, thiomorpholino-, S-oxothiomorpholino- or S,S-dioxothiomorpholino-lower alkoxy, cyano-lower alkoxy, carboxy-lower alkoxy, lower alkoxycarbonyl-lower alkoxy, carbamoyl-lower alkoxy or N-mono-, or N,N-di-lower alkylcarbamoyl-lower alkoxy, or together with $R_9$ is lower alkylenedioxyl or a fused-on benzo or cyclohexeno ring, $R_9$ together with $R_8$ is lower alkylenedioxy or a fused-on benzo or cyclohexeno ring, or is hydrogen, lower alkyl, hydroxy, lower alkoxy or cycloalkoxy, or a salt thereof.

2. A compound according to claim 1 of formula Ib wherein $R_2$ is lower alkyl, 3- to 5-membered cycloalkyl-lower alkyl or cycloalkyl, $R_3$ is carboxy, lower alkoxycarbonyl, formyl or hydroxymethyl, $R_4$ is lower alkoxycarbonyl or unsubstituted or lower alkyl-, lower alkoxy-, nitro- and/or halo-substituted α-phenyl-lower alkoxycarbonyl, $R_5$ and $R_6$ are hydrogen, $R_7$ is lower alkyl, lower alkoxy-lower alkyl, lower alkoxy-lower alkoxy, lower alkoxy-lower alkoxy-lower alkyl, unsubstituted or lower alkyl-, lower alkoxy-, hydroxy-, halo-, nitro- and/or amino-substituted phenyl-lower alkoxy, optionally N-oxidised pyridyl-lower alkoxy, lower alkylthio-lower alkoxy, lower alkanesulfonyl-lower alkoxy, lower alkanoyl-lower alkoxy, optionally N-oxidised pyridyl-lower alkoxy, cyano-lower alkoxy, carboxy-lower alkoxy, lower alkoxycarbonyl-lower alkoxy, carbamoyl-lower alkoxy, lower alkylcarbamoyl-lower alkoxy or di-lower alkylcarbamoyl-lower alkoxy, $R_8$ is hydrogen, lower alkyl, hydroxy, lower alkoxy or polyhalo-lower alkoxy or together with $R_9$ is lower alkylenedioxy, and $R_9$ is hydrogen or together with $R_8$ is lower alkylenedioxy, or a salt thereof.

3. A compound according to claim 1 of formula Ib wherein $R_2$ is branched $C_1$–$C_4$alkyl or 3- to 5-membered cycloalkyl-$C_1$–$C_4$alkyl, $R_3$ is carboxy, $C_1$–$C_4$alkoxycarbonyl, formyl or hydroxymethyl, $R_4$ is $C_1$–$C_4$alkoxycarbonyl or α-phenyl-$C_1$–$C_4$alkoxycarbonyl, $R_5$ and $R_6$ are hydrogen, $R_7$ is $C_1$–$C_4$alkyl, $C_1$–$C_4$alkoxy-$C_1$–$C_4$alkyl, $C_1$–$C_4$alkoxy-$C_1$–$C_4$alkoxy, $C_1$–$C_4$alkoxy-$C_1$–$C_4$alkoxy-$C_1$–$C_4$alkyl, phenyl-$C_1$–$C_4$alkoxy, pyridyl-$C_1$–$C_4$alkoxy, $C_1$–$C_4$alkylthio-$C_1$–$C_4$alkoxy, $C_1$–$C_4$alkanesulfonyl-$C_1$–$C_4$alkoxy, $C_1$–$C_4$alkanoyl-$C_1$–$C_4$alkoxy, $C_1$–$C_4$alkoxycarbonyl-$C_1$–$C_4$alkoxy, carbamoyl-$C_1$–$C_4$alkoxy or di-$C_1$–$C_4$alkylcarbamoyl-$C_1$–$C_4$alkoxy, $R_8$ is hydrogen, $C_1$–$C_4$alkyl, hydroxy or $C_1$–$C_4$alkoxy or together with $R_9$ is $C_1$–$C_4$alkylenedioxyl, and $R_9$ is hydrogen or together with $R_8$ is $C_1$–$C_4$alkylenedioxy, or a salt thereof.

4. A compound according to claim 1 of formula Ib wherein $R_2$ is branched $C_1$–$C_4$alkyl, $R_3$ is carboxy, formyl or hydroxymethyl, $R_4$ is $C_1$–$C_4$alkoxycarbonyl, $R_5$, $R_6$ and $R_9$ are hydrogen, $R_7$ is $C_1$–$C_4$alkoxy-$C_1$–$C_4$alkoxy or $C_1$–$C_4$alkoxy-$C_1$–$C_4$alkyl, and $R_8$ is hydrogen, $C_1$–$C_4$alkyl or $C_1$–$C_4$alkoxy, or a salt thereof.

5. A compound as claimed in claim 1 being 2(S)-Amino-4(S)-[4-methoxy-3-(3-methoxypropoxy)-benzyl]-5-methyl-hexanoic acid ethyl ester, 2(S)-(Tert-butoxycarbonyl)amino-4(S)-[4-methoxy-3-(3-methoxypropoxy)-benzyl]-5-methyl-hexanoic acid ethyl ester, 2(S)-(Tert-butoxycarbonyl)amino-4(S)-(p-tert-butylphenyl)-5-methyl-hexanoic acid ethyl ester, 2(S)-(Tert-butoxycarbonyl)amino-4(R)-(p-tert-butylbenzyl)-hexanoic acid ethyl ester, 2(S)-(Tert-butoxycarbonyl)amino-4(S)-[4tert-butyl-3-(3-methoxypropoxy)-benzyl]-5-ethyl-hexanoic acid ethyl ester, 2(S)-(Tert-butoxycarbonyl)amino-4(S)-[3-benzyloxy-4,5-ethylenedioxy-benzyl]-5-methyl-hexanoic acid ethyl ester, 2(S)-(Tert-butoxycarbonyl)amino-4(S)-[4-ethyl-3-(3-methoxypropoxy)-benzyl]-5-methyl-hexanoic acid ethyl ester, 2(S)-(Tert-butoxycarbonyl)amino-4(S)-[3-benzyloxy-4-methoxy-benzyl]-5-methyl-hexanoic acid ethyl ester, 2(S)-(Tert-butoxycarbonyl)amino-4(S)-[4-benzyloxy-3-(3-methoxy-propoxy)-benzyl]-5-methyl-hexanoic acid ethyl ester, 2(S)-(Tert-butoxycarbonyl)amino-4(S)-benzyloxymethyl-5-methyl-hexanoic acid ethyl ester, 2(S) -(Tert-butoxycarbonyl)amino-4(S)-[4-methoxy-3-(3-methoxypropoxy)-benzyl]-5-methyl-hexan-1-ol, 2(S)-Tert-butoxycarbonyl)amino-4(S)-[4-methoxy-3-(3-methoxypropoxy)-benzyl]-5-methyl-hexanal, 2(S)-(Tert-butoxycarbonyl)amino-4(S)-(p-tert-butyl-benzyl)-5-methyl-hexanal, 2(S)-(Tert-butoxycarbonyl)amino-4(R)-(p-tert-butyl-benzyl)-hexanal, 2(S)-(Tert-butoxycarbonyl)amino-4(S)-[4-tert-butyl-3-(3-methoxypropoxy)-benzyl]-5-methyl-hexanal, 2(S)-(Tert-butoxycarbonyl)amino-4(S)-[3-benzyloxy-4,5-ethylenedioxy-benzyl]-5-methyl-hexanal, 2(S)-(Tert-butoxycarbonyl)amino-4(S)-[4-ethyl-3-(3-methoxypropoxy)-benzyl]-5-methyl-hexanal, 2(S)-(Tert-butoxycarbonyl)amino-4(S)-[4-methoxy-3-benzyloxy-benzyl]-5-methyl-hexanal, or 2(S)-(Tert-butoxycarbonyl)amino-4(S)-[4-benzyloxy-3-(3-methoxy-propoxy)-benzyl]-5-methyl-hexanal, or a salt thereof.

* * * * *